(12) United States Patent
Stout et al.

(10) Patent No.: US 8,574,203 B2
(45) Date of Patent: *Nov. 5, 2013

(54) SYSTEMS AND METHODS FOR PROVIDING A FLUSHABLE CATHETER ASSEMBLY

(75) Inventors: Marty L. Stout, South Jordan, UT (US); Weston F. Harding, Lehi, UT (US); S. Ray Isaacson, Roy, UT (US); Jonathan K. Burkholz, Salt Lake City, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 120 days.

This patent is subject to a terminal disclaimer.

(21) Appl. No.: 13/042,103

(22) Filed: Mar. 7, 2011

(65) Prior Publication Data
US 2011/0160662 A1    Jun. 30, 2011

Related U.S. Application Data

(63) Continuation-in-part of application No. 12/703,336, filed on Feb. 10, 2010, now Pat. No. 8,469,928, and a continuation-in-part of application No. 12/544,625, filed on Aug. 20, 2009, now Pat. No. 8,388,583.

(60) Provisional application No. 61/364,576, filed on Jul. 15, 2010, provisional application No. 61/151,775, filed on Feb. 11, 2009.

(51) Int. Cl.
*A61M 5/00* (2006.01)

(52) U.S. Cl.
USPC ............ 604/244; 604/246; 604/284; 604/533

(58) Field of Classification Search
USPC ............. 604/164.01, 164.02, 167.01–167.06, 604/168.01, 244–246, 249, 284, 533
See application file for complete search history.

(56) References Cited

U.S. PATENT DOCUMENTS

| 4,387,879 A | 6/1983 | Tauschinski |
|---|---|---|
| 4,449,693 A | 5/1984 | Gereg |

(Continued)

FOREIGN PATENT DOCUMENTS

| CA | 2 133 053 A1 | 3/1995 |
|---|---|---|
| CA | 2133053 A1 | 3/1995 |

(Continued)

OTHER PUBLICATIONS

Silva, Elson, Email Regarding "Respecting Hydrology Science and IP Rights—US Pat. Application 20110130728," pp. 1-6, Jun. 2, 2011.

*Primary Examiner* — Theodore Stigell
(74) *Attorney, Agent, or Firm* — Jeanne Lukasavage; Craig Metcalf; Kirton McConkie

(57) ABSTRACT

A flushable catheter assembly having features to enable selective activation of fluid flow through the catheter assembly is disclosed herein. A septum is placed within the catheter adapter of the catheter assembly and includes a pathway that is closed prior to being biased open via a septum activator also positioned within the catheter adapter. A plurality of air vent channels is interposed between the septum and the inner surface of the catheter adapter to permit "flashback" of blood during insertion of the catheter into a patient. The septum activator is advanced through the pathway of the septum as a coupler is attached to a proximal opening of the catheter adapter.

20 Claims, 27 Drawing Sheets

(56) References Cited

U.S. PATENT DOCUMENTS

| | | |
|---|---|---|
| 4,758,225 A | 7/1988 | Cox et al. |
| 4,842,591 A | 6/1989 | Luther |
| 4,874,377 A | 10/1989 | Newgard et al. |
| 4,917,668 A | 4/1990 | Haindl |
| 4,935,010 A | 6/1990 | Cox et al. |
| 4,950,257 A | 8/1990 | Hibbs et al. |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard et al. |
| 5,084,023 A | 1/1992 | Lemieux |
| 5,085,645 A * | 2/1992 | Purdy et al. ............. 604/167.03 |
| 5,108,374 A | 4/1992 | Lemieux |
| 5,127,905 A | 7/1992 | Lemieux |
| 5,154,703 A | 10/1992 | Bonaldo |
| 5,156,596 A | 10/1992 | Balbierz et al. |
| 5,234,410 A | 8/1993 | Graham et al. |
| 5,290,246 A | 3/1994 | Yamamoto et al. |
| 5,295,969 A | 3/1994 | Fischell et al. |
| 5,330,435 A | 7/1994 | Vaillancourt |
| 5,350,363 A | 9/1994 | Goode et al. |
| 5,352,205 A | 10/1994 | Dales et al. |
| 5,405,323 A | 4/1995 | Rogers et al. |
| 5,456,675 A | 10/1995 | Wolbring et al. |
| 5,487,728 A | 1/1996 | Vaillancourt |
| 5,520,666 A | 5/1996 | Choudhury et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,651,772 A | 7/1997 | Arnett |
| 5,657,963 A | 8/1997 | Hinchliffe et al. |
| 5,697,915 A | 12/1997 | Lynn |
| 5,738,144 A | 4/1998 | Rogers |
| 5,749,861 A | 5/1998 | Guala et al. |
| 5,806,831 A | 9/1998 | Paradis |
| 5,817,069 A | 10/1998 | Arnett |
| 5,911,710 A | 6/1999 | Barry et al. |
| 5,954,698 A | 9/1999 | Pike |
| 5,967,490 A | 10/1999 | Pike |
| 6,039,302 A | 3/2000 | Cote, Sr. et al. |
| 6,077,244 A | 6/2000 | Botich et al. |
| 6,117,108 A | 9/2000 | Woehr et al. |
| 6,171,287 B1 | 1/2001 | Lynn et al. |
| 6,273,869 B1 | 8/2001 | Vaillancourt |
| 6,485,473 B1 | 11/2002 | Lynn |
| 6,575,960 B2 | 6/2003 | Becker et al. |
| 6,595,981 B2 | 7/2003 | Huet |
| 6,699,221 B2 | 3/2004 | Vaillancourt |
| 6,719,726 B2 | 4/2004 | Meng et al. |
| 6,740,063 B2 | 5/2004 | Lynn |
| 6,883,778 B1 | 4/2005 | Newton et al. |
| 7,008,404 B2 * | 3/2006 | Nakajima ................. 604/158 |
| 7,347,839 B2 | 3/2008 | Hiejima |
| 7,396,346 B2 | 7/2008 | Nakajima |
| 7,470,254 B2 | 12/2008 | Basta et al. |
| 7,736,339 B2 | 6/2010 | Woehr et al. |
| 7,914,494 B2 | 3/2011 | Hiejima |
| 8,388,583 B2 * | 3/2013 | Stout et al. ............... 604/244 |
| 2006/0163515 A1 | 7/2006 | Ruschke |
| 2007/0083157 A1 | 4/2007 | Belley et al. |
| 2007/0083162 A1 | 4/2007 | O'Reagan et al. |
| 2007/0233007 A1 | 10/2007 | Adams |
| 2008/0039796 A1 | 2/2008 | Nakajima |
| 2008/0108944 A1 | 5/2008 | Woehr et al. |
| 2010/0204675 A1 | 8/2010 | Woehr et al. |
| 2010/0222746 A1 | 9/2010 | Burkholz |

FOREIGN PATENT DOCUMENTS

| | | |
|---|---|---|
| DE | 20 2009 009 602 U1 | 12/2009 |
| EP | 1 679 043 A1 | 7/2006 |
| WO | 99/34849 | 7/1999 |
| WO | WO 99/34849 | 7/1999 |
| WO | 2008/052790 A2 | 5/2008 |
| WO | 2009/114833 A1 | 9/2009 |

* cited by examiner

US 8,574,203 B2

SYSTEMS AND METHODS FOR PROVIDING A FLUSHABLE CATHETER ASSEMBLY

RELATED APPLICATIONS

The present application claims the benefit of U.S. Provisional Patent Application Ser. No. 61/364,512, filed Jul. 15, 2010, and entitled BLOOD CONTROL VALVE INTEGRAL TO CLOSED IV CATHETER SYSTEM OR ANY FEMALE LUER CONNECTOR, which is incorporated herein in its entirety. Further, the present application is a continuation-in-part of U.S. patent application Ser. No. 12/703,336, filed Feb. 10, 2010, and entitled SYSTEMS AND METHODS FOR PROVIDING A FLUSHABLE CATHETER ASSEMBLY, which claimed the benefit of U.S. Provisional Application No. 61/151,775, filed Feb. 11, 2009, and entitled CATHETER VALVE ASSEMBLY, and which was also a continuation-in-part of U.S. Pat. No. 8,388,583 "SYSTEMS AND METHODS FOR PROVIDING A FLUSHABLE CATHETER ASSEMBLY," issued Mar. 5, 2013, all of which are incorporated herein in their entireties.

BACKGROUND OF THE INVENTION

The current invention relates to infusion devices, specifically to peripheral intravenous (IV) catheters. In particular, the invention relates to a flushable peripheral IV catheter assembly having features to enable selective activation of fluid flow through the catheter assembly.

Catheters are commonly used for a variety of infusion therapies. For example, catheters are used for infusing fluids, such as normal saline solution, various medicaments, and total parenteral nutrition into a patient, withdrawing blood from a patient, as well as monitoring various parameters of the patient's vascular system.

Catheters or needles are typically coupled to a catheter adapter to enable attachment of IV tubing to the catheter. Thus, following placement of the catheter or needle into the vasculature of a patient, the catheter adapter is coupled to a fluid source via a section of IV tubing. In order to verify proper placement of the needle and/or catheter in the blood vessel, the clinician generally confirms that there is "flashback" of blood in a flashback chamber of the catheter assembly.

Once proper placement of the catheter is confirmed, the clinician must then attach the catheter adapter to a section of IV tubing. This process requires the clinician to manually occlude the vein to prevent undesirable exposure to blood. Manual occlusion of the patient vein requires the clinician to awkwardly maintain pressure on the vein of the patient while simultaneously coupling the catheter adapter and the IV tubing.

A common, yet undesirable practice is to permit blood to temporarily and freely flow from the catheter adapter while the clinician locates and couples the IV tubing to the catheter adapter. Another common practice is to attach the catheter adapter to the IV tubing prior to placing the needle or catheter into the vein of the patient. While this method may prevent undesirable exposure to blood, positive pressure within the IV line may also prevent desirable flashback.

Complications associated with infusion therapy include significant morbidity and even mortality. Such complications may be caused by regions of stagnant fluid flow within the vascular access device or nearby areas of the extravascular system. These are regions in which the flow of fluid is limited or non-existent due to the conformation of the septum or valve mechanism in the extravascular system or the fluid dynamics within that area of the extravascular system. Blood, air bubbles or infused medications may become trapped within these regions of stagnant flow as a result of the limited or non-existent fluid flow. When blood is trapped within the extravascular system bacteria can breed which can lead to infections. When a different medication is infused into the extravascular system, or the extravascular system is exposed to physical trauma, the extravascular system's fluid flow may become altered, releasing trapped air bubbles or residual medications back into the active fluid path of the extravascular system. This release of air bubbles and residual medication into the active fluid path extravascular system may result in significant complications.

Released air bubbles may block fluid flow through the extravascular system and prevent its proper functioning. More seriously, released air bubbles may enter the vascular system of the patient and block blood flow, causing tissue damage and even stroke. In addition, residual medications may interact with presently infused medications to cause precipitates within the extravascular system and prevent its proper functioning. Furthermore, residual medications may enter the vascular system of the patient and cause unintended and/or undesired effects.

Accordingly, there is a need in the art for a catheter assembly that permits controlled, desirable flashback without the risk of encountering undesirable exposure to blood. Furthermore, there is a need in the art to provide a valve mechanism in a catheter assembly that eliminates, prevents, or limits regions of stagnant flow within vascular access devices and extravascular system to provide better flush properties. Such a catheter assembly is disclosed herein.

BRIEF SUMMARY OF THE INVENTION

In order to overcome the limitations discussed above, the present invention relates to a flushable peripheral IV catheter assembly having features to enable selective activation of fluid flow through the catheter assembly. The catheter assembly of the present invention generally includes a catheter coupled to a catheter adapter. The catheter generally includes a metallic material, such as titanium, surgical steel or an alloy as is commonly known in the art. In some embodiments, a polymeric catheter may be used in combination with a metallic introducer needle, as is commonly known and used in the art.

In some embodiments of the present invention, a septum is positioned within a lumen of the catheter assembly to prevent or limit flow of a fluid through the catheter adapter. The septum generally includes a flexible or semi-flexible material that is compatible with exposure to blood, medicaments, and other fluids commonly encountered during infusion procedures. In some embodiments, a groove is provided on an inner surface of the catheter adapter, wherein the septum is seated within the groove. As such, the position of the septum within the catheter adapter is maintained.

In some implementations of the present invention, a closed or partially closed pathway, such as a slit or small hole is further provided in a barrier surface of the septum. The pathway permits fluid to bypass the septum and flow though the catheter adapter. In some embodiments, the pathway is a slit that is closed prior to being opened or activated by a probe or septum activator positioned within the lumen of the catheter adapter. Prior to being opened or activated, the slit prevents passage of fluid through the catheter adapter. Thus, in some embodiments a plurality of air vent channels are interposed between the septum and the groove to permit air flow through the catheter adapter prior to the slit being opened. The air vents prevent buildup of positive pressure within the catheter adapter thereby permitting flashback of blood into the catheter and a forward chamber of the catheter adapter.

The septum activator generally includes a plastic or metallic tubular body having a probing end and a contact end. The probing end is positioned adjacent to the pathway of the septum, and the contact end is positioned adjacent to a proximal opening of the catheter adapter. The probing end of the septum activator is advanced through the pathway of the septum when a probe is inserted into the proximal opening of the catheter adapter. As the probe contacts the contact surface of the septum activator, the septum activator is advanced in a distal direction through the catheter adapter whereupon the probing end of the septum activator opens the pathway through the septum. Once opened, free flow of fluid is enabled through the catheter assembly.

Finally, the presence of the septum activator within the lumen of the catheter adapter may result in aberrant fluid flow leading to undesirable stagnation and coagulation of fluids within the catheter assembly. Thus, in some embodiments of the present invention the septum activator further includes various flow deflectors and/or flow diversion channels to maintain proper fluid flow within the catheter adapter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

The term "proximal" is used to denote a portion of a device which, during normal use, is nearest the user and furthest from the patient. The term "distal" is used to denote a portion of a device which, during normal use, is farthest away from the user wielding the device and closest to the patient. The term "activation" of valve mechanism or septum is used to denote the action of opening or closing of such valve.

Figure 1:
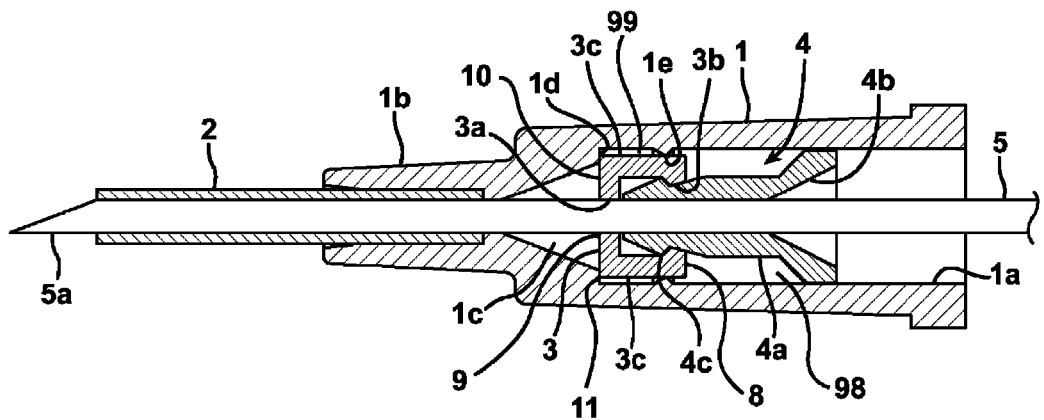
FIG. 1 is a cross-sectioned view of an indwelling catheter having a PRIOR ART flow control valve mechanism.

An example of a prior art extravascular system is disclosed in U.S. Pat. No. 7,008,404 and shown in FIGS. 1 to 3. An indwelling catheter has, as shown in FIG. 1, a hollow catheter body 1, a catheter 2 fitted into a holder 1b provided at a distal end of the catheter body 1, a septum 3 fitted inside the catheter body 1, and a hollow pusher 4 slidably fitted inside the catheter body 1. The catheter tube 2, septum 3, and the pusher 4 are coaxially aligned in this order.

The catheter body 1 has a tubular shape. An inner surface 1a is tapered toward the distal end, with a gradually reduced diameter. The catheter body 1 is preferably of a transparent or semi-transparent material so as to show the interior, enabling checking of movement inside. Suitable materials for catheter body 1 include, but are not limited to, thermoplastic polymeric resins such as polycarbonate, polystyrene, polypropylene and the like.

The catheter 2 is press-fitted into the tube holder 1b which communicates at its proximal end with the inside of the catheter body 1. It is preferred that a lubricating coating is provided to the entirety or part of the catheter 2 so as to reduce resistance caused by insertion through skin or into a blood vessel. Suitable materials for catheter 2 include, but are not limited to, thermoplastic resins such as fluorinated ethylene propylene (FEP), polytetrafluoroethylene (PTFE), polyurethane and the like. Preferably, catheter 2 is formed from a thermoplastic hydrophilic polyurethane that softens with exposure to physiological conditions present in the patient's body.

The septum 3 is of a generally tubular shape having a proximal end 8 and a membrane section 9 having a planar flat surface 10 located at the distal end 11. Typically, septum 3 further includes a single needle slit 3a or valve aperture located about the centre of membrane section 9, extending through membrane section 9, to facilitate penetration of septum 3 by introducer needle 5. The opposing slit surfaces of the needle slit 3a are designed to closely conform to the shape of introducer needle 5 during storage and prevent an outflow of fluid during and following removal of the introducer needle 5, then to seal upon removal of the introducer needle 5. With the pusher 4 inserted therethrough, slit 3a expands forward in the distal direction and opens, providing fluid communication between the catheter 2 and the rear of the catheter body 1. An annular protrusion 3b is provided on the inner surface of a rear opening of the septum 3, to engage shoulder 4c at the distal end of the pusher 4 so as to limit the movement of pusher 4 in the proximal direction and prevent the dislocation of the pusher 4 from septum 3. A plurality of gaps 3c are defined between an outer periphery of the septum 3 and the inner surface 1a of the catheter body 1. Distal and proximal spaces divided by the septum 3 communicate with each other through the gaps 3c. Thus the septum 3 slides smoothly with air passing through the gaps 3c.

The pusher 4 is typically made from a rigid thermoplastic material or a like material, and has a lumen extending therethrough. The pusher 4 has a tubular portion 4a, a conical flange 4b connected to the rear proximal end of the tubular portion 4a, and a shoulder 4c protruding from an outer periphery of the tubular portion 4a. Thus an annular shaped interstitial space is created between tubular portion 4a and the inner surface 1a of the catheter body 1. The distal front end of the tubular portion 4a is chamfered to facilitate its penetration into slit 3a of the septum 3, and is slidably supported by the annular protrusion 3b of the septum 3. The conical flange 4b has a conical inner surface so as to facilitate insertion of the needle 5 thereinto. The peripheral surface of the flange 4b contacts the inner surface 1a of the catheter body 1 and serves to provide stability to the pusher 4 and maintain the coaxial position with respect to the catheter 2. However the peripheral surface of the flange 4b does not form a fluid seal with inner surface 1a.

The indwelling catheter is prepared for use in such a state as shown in FIG. 1 with the front end of the needle 5 protruding from the front end of the catheter 2. In this state, the needle 5 penetrates through the septum 3, providing water-tight connection therebetween, and thereby preventing leakage of blood.

Figure 2:
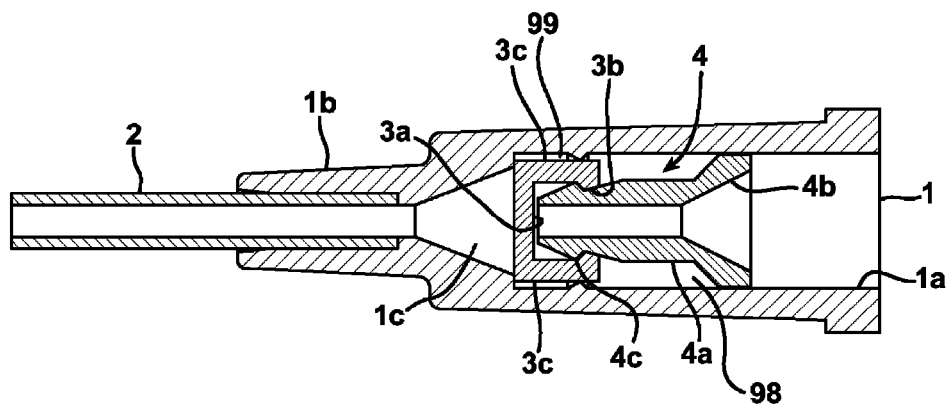
FIG. 2 is a cross-sectioned view of the PRIOR ART indwelling catheter of FIG. 1 following removal an introducer needle.

The indwelling catheter in this state is inserted into the body of a patient. Then, as shown in FIG. 2, the needle 5 is removed with the tube 2 retained in the body of the patient. Septum 3 maintains a fluid seal upon removal of needle 5, being retained catheter body 1 by an annular protrusion 1e. Pusher 4 is retained in a proximal position buy the interaction of annular protrusion 3b and shoulder 4c.

Figure 3:
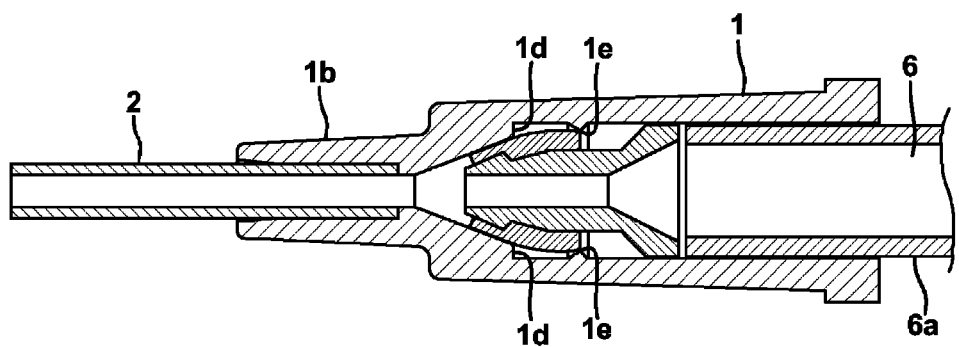
FIG. 3 is a cross-sectioned view of the PRIOR ART indwelling catheter of FIGS. 1 and 2 following insertion of a connector from a vascular access device.

A connector 6 (e.g. a luer connector) of a vascular access device is then inserted from the proximal end of the catheter body 1. When pressed into the catheter body 1, the connector 6 pushes at its distal end the pusher 4. The pusher 4 thus slides forward in distal direction to press at its distal end slit 3a of the septum 3 open thereby activating the flow control valve to the open position. The septum 3 is then pressed against the inner surface of a tapered cavity 1c of the catheter body 1 which stops the forward movement of pusher 4 at a distal position as shown in FIG. 3, thus providing communication between the catheter 2 and the vascular access device. The tapered inner surface 1a of the catheter body 1 allows for smooth insertion of the connector 6 and tight contact between an outer surface 6a of the connector 6 and the inner surface 1a through press fitting in order to prevent fluid leaking out of the proximal end of catheter body 1.

However, it should be noted that this valve mechanism has small interstitial spaces/areas within the catheter body 1 into which fluids can flow during use, which give rise to areas of low or no fluid flow. For example, in use, fluid can flow between the peripheral surface of the flange 4b and the inner surface 1a of catheter body 1 and into the interstitial space 98 between the outer periphery of tubular portion 4a and the inner surface 1a. In addition, fluid can flow into interstitial space 99 which is gap 3c between the outer periphery of septum 3 and the inner surface 1a of the catheter body 1. The low or no fluid flow that exists in spaces/areas 98 and 99 makes it very difficult to subsequently flush out any blood, medicament or air bubbles which may flow into these areas during use of the catheter.

Figure 4:
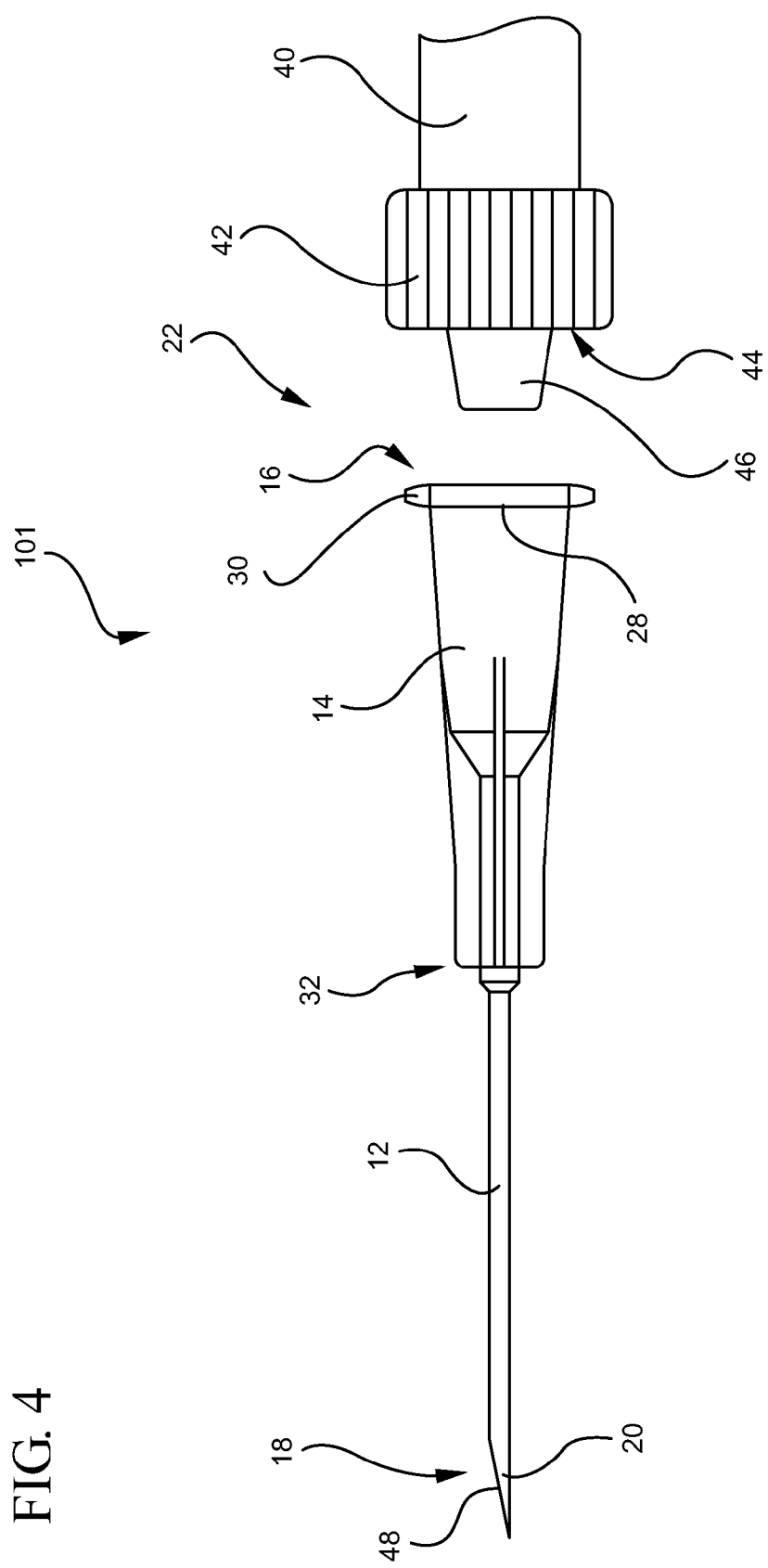
FIG. 4 is a perspective view of an embodiment of a catheter assembly in accordance with the present invention.

Referring now to FIG. 4, a catheter assembly 101 is illustrated. The catheter assembly 101 generally includes a catheter 12 coupled to a distal end 32 of a catheter adapter 14. The catheter 12 and the catheter adapter 14 are integrally coupled such that an internal lumen 16 of the catheter adapter 14 is in fluid communication with a lumen 18 of the catheter 12. The catheter 12 generally comprises a biocompatible material having sufficient rigidity to withstand pressures associated with insertion of the catheter into a patient. In some embodiments, the catheter 12 comprises a metallic material, such as titanium, stainless steel, nickel, molybdenum, surgical steel, and alloys thereof. In other embodiments, the catheter 12 comprises a rigid, polymer material, such as vinyl. A tip portion 20 of the catheter is generally configured to include a beveled cutting surface 48. The beveled cutting surface 48 is utilized to provide an opening in a patient to permit insertion of the catheter 12 into the vascular system of the patient.

The features of the catheter assembly may be incorporated for use with an over-the-needle catheter assembly. For example, a flexible or semi-flexible polymer catheter may be used in combination with a rigid introducer needle to enable insertion of the catheter into a patient. Surgically implanted catheters may also be used.

Once inserted into a patient, the catheter 12 and catheter adapter 14 provide a fluid conduit to facilitate delivery of a fluid to and/or retrieval of a fluid from a patient, as required by a desired infusion procedure. Thus, in some embodiments the material of the catheter 12 and the catheter adapter 14 are selected to be compatible with bio-fluids and medicaments commonly used in infusion procedures. Additionally, in some embodiments a portion of the catheter 12 and/or catheter adapter 14 is configured for use in conjunction with a section of intravenous tubing 40 to further facilitate delivery of a fluid to or removal of a fluid from a patient.

In some embodiments, a proximal end 22 of the catheter adapter 14 includes a flange 28. The flange 28 provides a positive surface which may be configured to enable coupling of an intravenous tubing or patient conduit 40 to the catheter assembly 101. In some embodiments, the flange 28 includes a set of threads 30. The threads 30 are generally provided and configured to compatibly receive a complementary set of threads 44 comprising a portion of a male luer or conduit coupler 42. The conduit coupler 42 is generally coupled to an end portion of the patient conduit 40 in a fluid-tight manner. In some embodiments, an inner portion of the conduit coupler 42 is extended outwardly to provide a probe surface 46.

Figure 8:
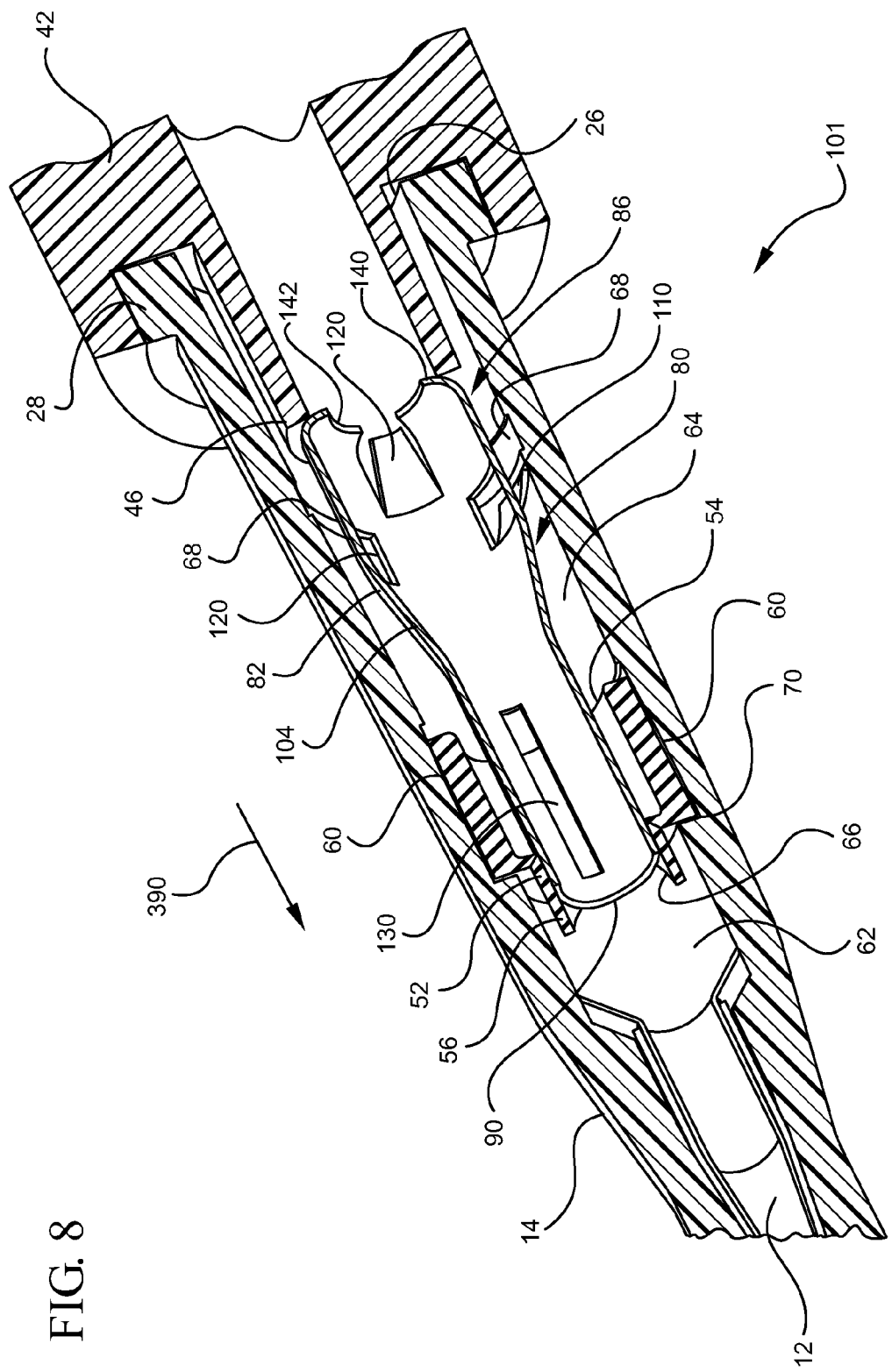
FIG. 8 is a cross-sectioned view of an assembled catheter assembly in accordance with the present invention, following activation.

The probe surface 46 is generally configured to compatibly insert within a proximal end 22 of the catheter adapter 14. Following insertion of the probe 46 into the proximal end 22 of the catheter adapter 14, the conduit coupler 42 is rotated to interlock the coupler 42 and the flange 28 (via the sets of threads 30 and 44). During the process of interlocking the coupler 42 and the flange 28, the probe 46 is advanced into the lumen 16 of the catheter adapter 14 to an inserted position (as shown in FIG. 8). The inserted position of the probe surface 46 activates the catheter assembly 101 to enable flow of fluid through the catheter 12 and catheter adapter 14. Once the conduit coupler 42 and the catheter adapter 14 are attached, a fluid may be delivered to a patient via the patient conduit 40 and the inserted catheter 12.

Figure 5A:
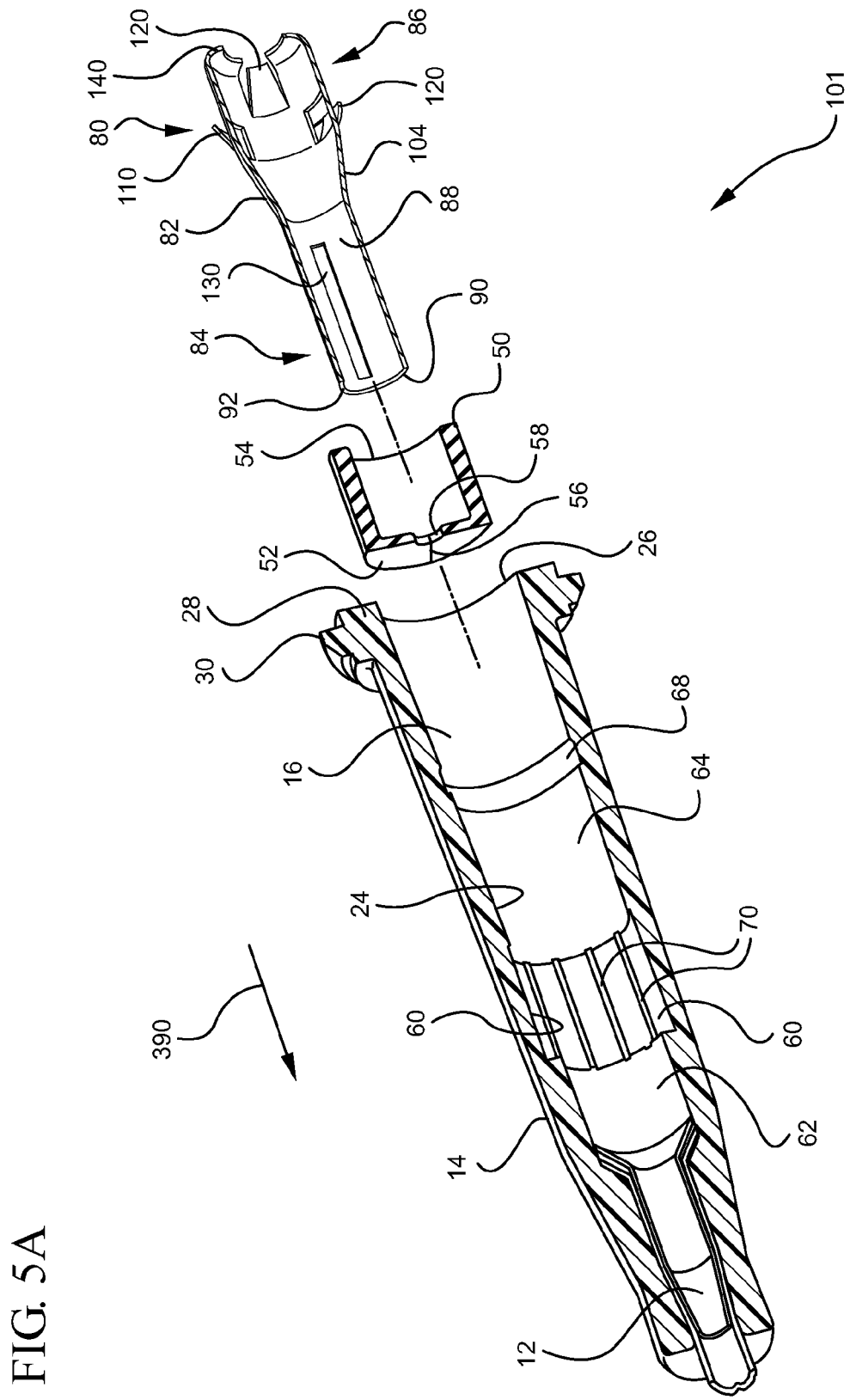
FIG. 5A is an exploded cross-sectioned view of a catheter assembly in accordance with the present invention.

Referring now to FIG. 5A, an exploded, cross-sectional view of a catheter assembly 101 is shown. In some embodiments, the catheter adapter 14 includes various design features and components to control and/or limit flow of fluid through the catheter assembly 101. For example, in some embodiments of the present invention a septum 50 is positioned within the inner lumen 16 of the catheter adapter 14. The septum 50 generally comprises a flexible, or semi-flexible polymer plug having an outer diameter that is configured to compatibly seat within a groove or channel 60 formed on an inner surface 24 of the catheter adapter 14. In some embodiments, the septum 50 is barrel shaped having a barrier surface 52 comprising a distal end of the septum 50 and further having an opening 54 comprising a proximal end of the septum 50. When positioned within the channel 60, the barrier surface 52 of the septum 50 divides the inner lumen 16 of the catheter adapter 14 into a forward fluid chamber 62 and a rearward fluid chamber 64. Thus, the presence of the septum 50 controls or limits passage of fluid between the forward and rearward fluid chambers 62 and 64. Specifically, a chosen configuration of the barrier surface 52 of the septum 50 largely determines the ability of a fluid to flow through the inner lumen 16 of the catheter adapter 14.

For example, in some embodiments the barrier surface 52 of the septum 50 is configured to include a slit 56. The slit 56 is configured to provide selective access or flow of a fluid through the barrier surface 52. In some embodiments, slit 56 is configured to remain in a closed, fluid-tight position until activated or opened by advancing a septum activator 80 through the slit 56 in a distal direction 390. In some embodiments, the barrier surface 52 comprises one slit 56. In other embodiments, the barrier surface 52 is modified to include multiple slits 56 and 66, as shown in FIG. 8.

For some infusion therapy techniques, it may be desirable to permit a controlled flow of fluid through the septum 50 prior to activating the septum 50 with the septum activator 80. Thus, in some embodiments the slit 56 further comprises a leak orifice 58. The leak orifice 58 is positioned in the barrier surface 52 and comprises an opening diameter calculated to permit controlled flow of liquid or air between the forward and rearward chambers 62 and 64. In some embodiments, the barrier surface 52 is modified to include a single leak orifice 58. In other embodiments, the barrier surface 52 is configured to include multiple leak orifices. Still, in other embodiments the barrier surface 52 does not include a slit 56, but rather includes at least one leak orifice 58. For these embodiments, the septum 50 generally comprises an elastic material such that when the septum activator 80 is advanced in a distal direction 390, a leading edge 92 of the septum activator 80 contacts the barrier surface 52 and stretches the leak orifice 58 to provide a larger orifice thereby permitting increased flow of air and/or fluid through the catheter adapter 14.

The groove or channel 60 into which the septum is seated comprises a recessed portion of the inner surface 24 of the catheter adapter 14. The outer diameter of the septum 50 is generally configured to compatibly and securely seat within the channel 60. For example, in some embodiments the outer diameter of the septum 50 is selected to be both slightly smaller than the diameter of the channel 60 and slightly larger than the diameter of the inner lumen 16. As such, the septum 50 is retained within the channel 60 during use of the catheter assembly 101.

For some infusion therapy techniques, air flow between the forward and rearward chambers 62 and 64 may be desirable. For example, for those embodiments comprising a septum 50 having a fluid-tight slit 56, passage of air from the forward chamber 62 to the rearward chamber 64 is prohibited prior to opening or activating the septum 50 via the septum activator 80, as previously discussed. Thus, when the catheter 12 of the catheter assembly 101 is inserted into the vascular system of a patient, a positive pressure develops within the forward chamber 62 thereby preventing a desired flashback of the patient's blood into the catheter adapter 14. An observable flashback is generally desirable to confirm accurate placement of the catheter tip 20 within the vein of the patient. Thus, some embodiments of the present invention include features or elements to enable airflow between the forward chamber 62 and the rearward chamber 64, without requiring activation of the septum 50 with the septum activator 80. As such, some embodiments of the present invention provide an observable flashback, as generally desired for infusion procedures.

For example, in some embodiments the barrier surface 52 of the septum 50 is modified to include leak orifice 58, as previously discussed. In other embodiments, a plurality of air vent channels 70 is interposed between the septum 50 and the inner surface 24 of the catheter adapter 14. The air vent channels 70 relieve the positive pressure within the forward chamber 62 by providing an access for air to bypass the septum 50 into the rearward chamber 64. In some embodiments, the air vent channels 70 are constructed by removing portions of the channel 60 surface, resulting in a plurality of generally parallel grooves.

In addition to permitting air flow between the forward and rearward chambers 62 and 64, the vent channels 70 may be configured to permit fluid to flow through the catheter adapter 14 prior to activating or opening the slit 56 with the septum activator 80. In some embodiments, the rate at which air and/or fluid flows between the forward and rearward chambers 62 and 64 is adjusted by manufacturing the catheter adapter 14 to include a greater or lesser number of vent channels 70. In other embodiments, the rate at which air and/or fluid flows between the forward and rearward chambers 62 and 64 is adjusted by manufacturing the catheter adapter 14 to include vent channels 70 having a greater or lesser cross-sectioned area. Thus, in some embodiments the rate at which air and/or fluid flows between the forward and rearward chambers 62 and 64 is increased by manufacturing a catheter adapter 14 having either an increased number of vent channels 70, or vent channels 70 having a greater cross-sectioned area. Conversely, in other embodiments the rate at which air and/or fluid flows between the forward and rearward chambers 62 and 64 is decreased by manufacturing a catheter adapter 14 having either a decreased number of vent channels 70, or vent channels 70 having a lesser cross-sectioned area.

With continued reference to FIG. 5A, the septum activator 80 comprises a probe-like structure that is primarily housed in the rearward chamber 64 of the catheter adapter 14. The septum activator 80 generally comprises a tubular body 82 having a distal end 84 and a proximal end 86. The tubular body 82 comprises a rigid or semi-rigid material, such as a plastic or metallic material. The tubular body 82 further comprises an inner lumen 88 for facilitating flow of a fluid and/or liquid through the septum activator 80.

The distal end 84 of the tubular body 82 is configured to compatibly insert within the opening 54 of the septum 50. The distal end 84 further includes a probing surface 90 which extends through the opening 54 of the septum 50 to a position proximal to the barrier surface 52 of the septum 50, as shown in FIG. 8. The probing surface 90 is advanced through the slit 56 and 66, or through the leak orifice 58 as the septum activator is advanced through the catheter adapter 14 in a distal direction 390. Advancement of the septum activator 80 through the catheter adapter 14 will be discussed in detail below, in connection with FIGS. 7 and 8.

Still, in other embodiments the septum 50 is coated with a hydrophobic coating, or a polymeric swelling coating to repel or prevent fluid from flowing through the vent channels 70. A hydrophobic coating is generally selected to reduce the surface energy of the septum 50 and/or adapter 14 to inhibit blood wicking into the air vents 70. In some embodiments, a surface of the septum 50 or catheter adapter 14 is coated with a polyxylylene polymer material, such as parylene. Parylene is a chemically resistant coating with good barrier properties for inorganic and organic fluids, strong acids, caustic solutions, gases and water vapors. In some embodiments, a parylene coating is applied to the outer surface of the septum 50 via vapor deposition. In other embodiments, a polyxylylene polymer coating is applied to a vent channel 70 via vapor deposition.

In some embodiments, a dehydrated polymer material is applied to a surface of the septum 50 or catheter adapter 14 which comprises the vent channels 70. A dehydrated polymer is generally selected to expand or swell upon contact with fluid. As such, when the dehydrated polymer swells, a flow through the vent channels 70 is blocked or occluded by the swollen polymer. Initially, the dehydrated polymer generally comprises a thin profile prior to exposure to moisture. However, when exposed to moisture the polymer absorbs the moisture which increases the profile of the polymer to block flow through the vent 70. Therefore, by coating the septum 50 and/or catheter adapter 14 with a desired coating, flow of air is permitted between the forward and rearward chambers 62 and 64, yet fluid flow through the vent channels 70 is prevented.

Figure 5B:
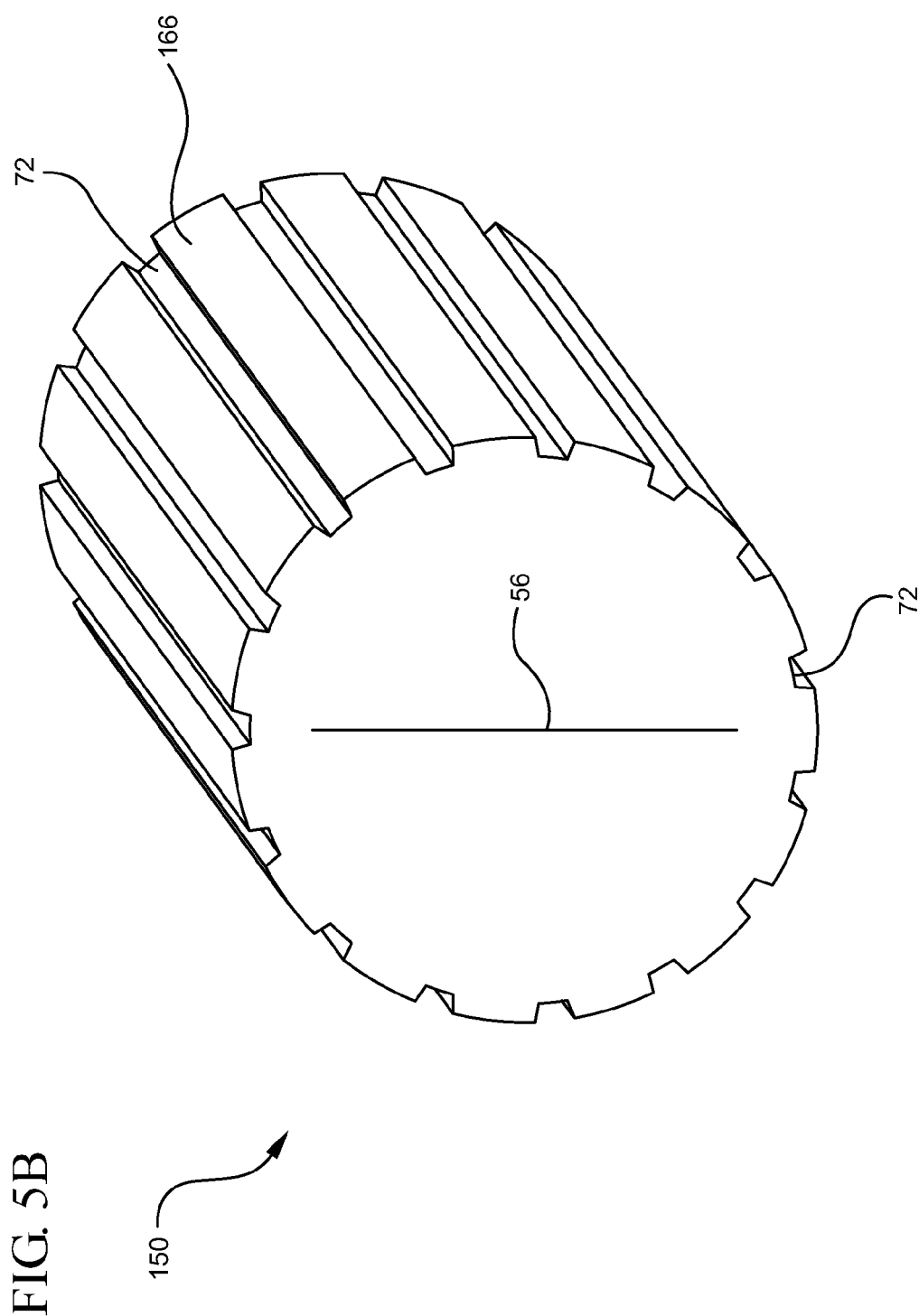
FIG. 5B is a perspective view of an embodiment of a septum in accordance with the present invention.

Referring now to FIG. 5B, an embodiment of a septum 150 is shown. In some embodiments, an outer surface 166 of the septum 150 is modified to include a plurality of recessed grooves 72. The recessed grooves 72 provide pathways between the forward and rearward chambers 62 and 64 through which air and/or fluid may flow. Thus, in some embodiments the channel 60 does not include air vent channels 70, but rather the outer surface 166 of the septum 150 is modified to provide desired flow between the forward and rearward chambers 62 and 64.

The blood pressure of the patient is largely responsible for the rate at which blood and air flows through the septum 50 and 150 of the catheter assembly 101. As such, the flow rate through the system is affected by the combined effective hydraulic diameter of all flow paths. Thus, in some embodiments the hydraulic diameter of the vent channels 70 and/or recessed grooves 72 are modified to increase or decrease the rate of flow through the catheter assembly 101. In other embodiments, the hydraulic diameter of the vent channels 70 and/or recessed grooves 72 are decreased thereby resulting in substantially reduced or stopped flow through the ventilation means. The governing equation for controlling the flow rate through the ventilation means is given in Equation 1, where BP is the blood pressure, A is the surface area of the ventilation means, ó is the surface tension of the blood, and P is the perimeter of the ventilation means.

$$BP(A) = ó(P)$$ Equation 1:

Thus, according to Equation 1, when the perimeter of the ventilation means is small, the ventilation means will allow air venting, but will prevent blood flow due to the relatively high surface tension (ó) of blood. However, when the perimeter of the ventilation means is increased, the surface tension between the blood and the vent is decreased thereby enabling the blood to slowly leak through the vents and around the septum to provide desirable, yet controlled flashback. Therefore, by adjusting the various variable of Equation 1, a desired flow will be achieved. Thus, based on the size and/or number of vents around the septum, the catheter assembly design will provide customized, controlled and predictable blood flow around the septum 50 or 150. In some embodiments, it is desirable to permit slow, controlled blood flow as a means for providing a visual indicator that the catheter is in the blood vessel, without the risk of immediate exposure to the blood. In other embodiments, it is desirable to only permit air to pass through the vents.

Figure 6A:
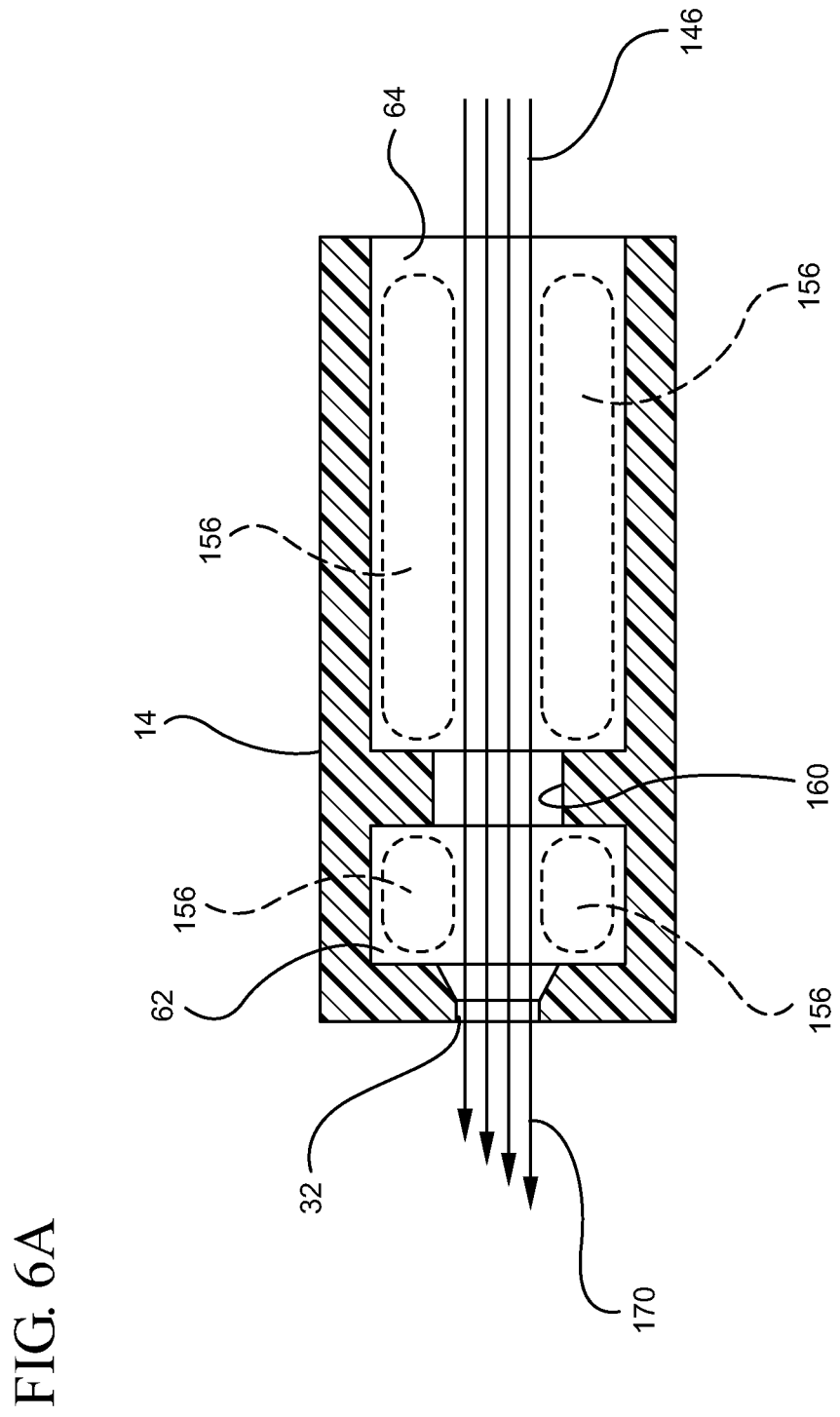
FIG. 6A is a cross-sectioned view of an interior lumen of a catheter adapter demonstrating fluid flow without the presence of a septum activator in accordance with a representative embodiment of the present invention.

Referring now to FIG. 6A, a cross-section view of an interior lumen of a catheter adapter 14 is shown. In some embodiments, catheter adapter 14 includes a forward fluid chamber 62 and a rearward fluid chamber 64 fluidly connected via a narrowed channel or port 160. As configured and in some embodiments, a fluid pathway 170 is defined whereby a fluid 146 flows downstream from the rearward fluid chamber 64, through the port 160 and into the forward fluid chamber 62. The fluid pathway 170 continues through the forward fluid chamber 62 and exits the distal end 32 into a catheter (not shown) or other downstream conduit. While fluid 146 fills the entire lumen of the catheter adapter 14, the fluid pathway 170 is generally restricted to a narrow pathway through a central portion of the cross-section of the catheter adapter 14. Accordingly, fluid 146 that is not part of the narrow fluid pathway 170 stagnates or circulates within dead zones 156. Fluid 146 trapped within these dead zones is prevented from sufficiently mixing with fluid 146 in the fluid pathway 170. In some embodiments, stagnation results in increased, localized concentrations of chemicals, bodily fluids and/or medicaments that may lead to precipitation, coagulation or administration of dangerously high doses of medications. Therefore, in some embodiments of the present invention, a septum activator 80 is provided having features to eliminate dead zones 156 within the catheter adapter 14 lumen.

Figure 6B:
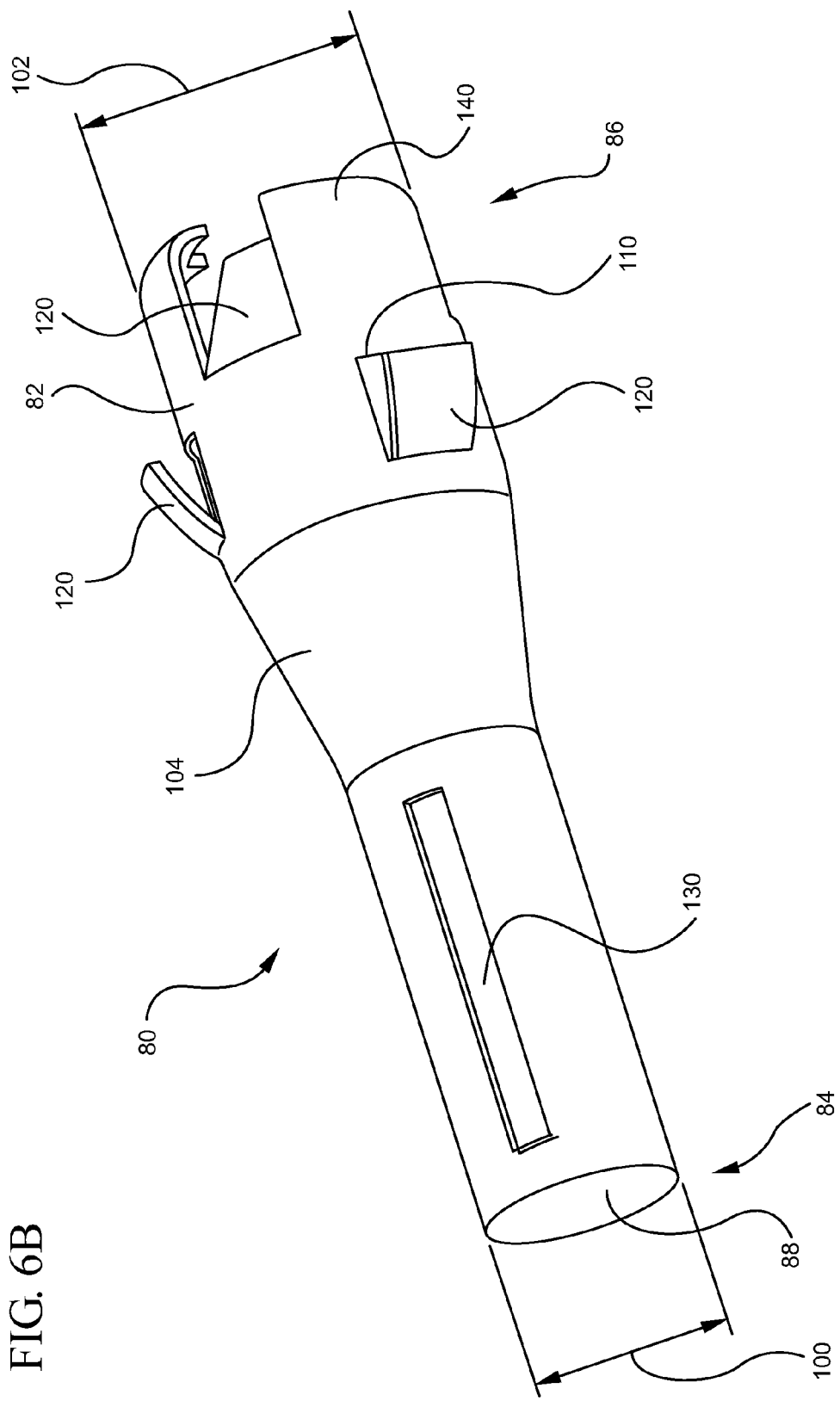
FIG. 6B is a perspective view of an embodiment of a septum activator in accordance with the present invention.

Referring now to FIG. 6B, a perspective view of the septum activator 80 is shown. In some embodiments, the distal end 84 of the tubular body 82 comprises a first diameter 100 that is less than a second diameter 102 of the proximal end 86. The narrower distal end 84 is configured to compatibly insert within the opening 54 of the septum 50, while the wider proximal end 86 is configured to compatibly seat within the rearward chamber 64 of the catheter adapter 14. In some embodiments, the septum activator further includes a tapered middle section 104 to couple the distal 84 and proximal 86 ends.

Figure 7:
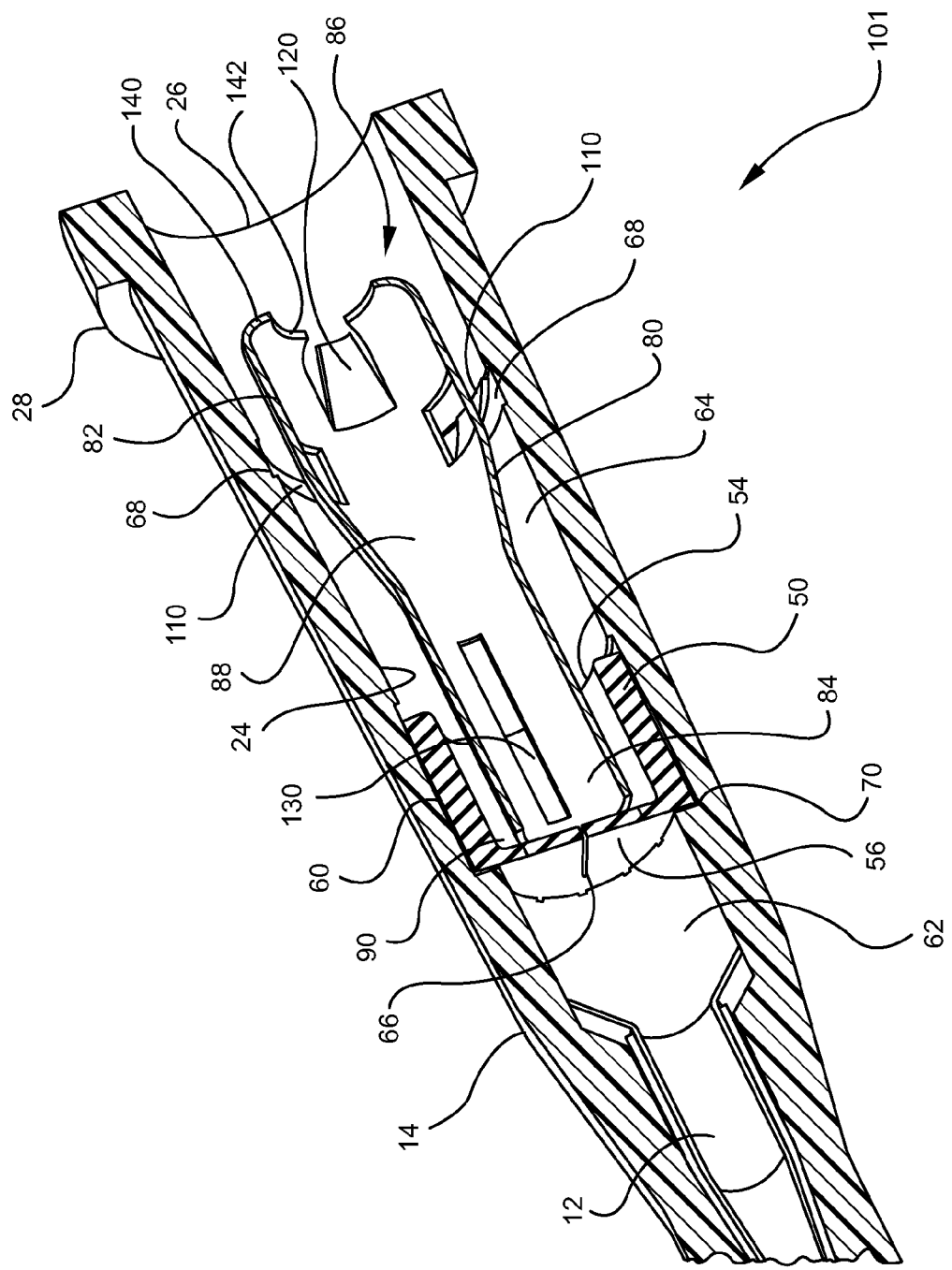
FIG. 7 is a cross-sectioned view of an assembled catheter assembly in accordance with the present invention, prior to activation.

In some embodiments, the proximal end 86 of the septum activator 80 further includes a retention spring 110. The retention spring 110 generally comprises an outwardly biased portion of the tubular body 82 configured to compatibly engage a septum activator retention groove 68, as shown in FIGS. 5A, and 7-8. The interaction between the retention spring 110 and the groove 68 limits the lateral movement of the septum activator 80 within the lumen 16 of the catheter adapter 14. Thus, the width of the retention groove 68 determines or limits the distance of travel for the septum activator 80 within the catheter adapter 14. Additionally, the interaction between retention spring 110 and the groove 68 prevents removal of the septum activator 80 from the catheter adapter 14. In some embodiments, the septum activator 80 comprises a plurality of retention springs 110, while in other embodiments the septum activator 80 comprises a single retention spring 110.

In some embodiments, the septum activator 80 further comprises features for directing or diverting fluid flow around and/or through the septum activator 80. Flow diversion may be important to prevent stagnation or coagulation of fluids within dead zones 156 of the septum activator 80 and/or the lumen 16 of the catheter adapter 14 resulting in blockages. Additionally, stagnation of fluid flow through the catheter assembly 101 may result in a build up of undesirable concentrations of medicaments within the catheter adapter 14 and/or the septum activator 80, as previously discussed. Undesirable high concentrations may result in ineffective treatment causing serious side effects, including death. Thus, in some embodiments the septum activator 80 is modified to include flow deflectors 120 and flow diversion channels 130 to provide a flushable catheter assembly 101 system.

The flow deflectors 120 generally comprise inwardly and outwardly angled portions of the septum activator 80 outer surface. The flow deflectors 120 are positioned so as to be protrude into a flow path through the catheter adapter 14. Thus, as the fluid contacts the flow deflectors 120 the path of the fluid flow is disturbed. This disturbance results in redirecting the fluid flow both through the inner lumen 88 of the septum activator 80, and between the outer surface of the septum activator 80 and the inner surface 24 of the catheter adapter 14. In some embodiment, the retention spring 110 also serves as a flow deflector 120.

A flow diversion channel 130 is provided to permit exchange of fluid between the lumen of the catheter adapter 16 and the inner lumen 88 of the septum activator 80. Thus, the flow diversion channel 130 prevents stagnation and/or clotting of fluid between the inner surface 24 of the catheter adapter 14 and the outer surface of the septum activator 80. In some embodiments, the flow diversion channel 130 comprises a window or opening in the surface of the tubular body 82. In other embodiments, the flow diversion channel 130 further comprises a flap or angled surface to further direct fluid to flow through the channel 130.

The proximal end 86 of the septum activator 80 further includes a contact surface 140. The contact surface 140 comprises the most proximal end portion of the septum activator 80 and is positioned within the rearward chamber 64 of the catheter adapter 14 adjacent to the proximal opening 26 of the catheter adapter 14, as shown in FIG. 7, below.

Figure 6C:
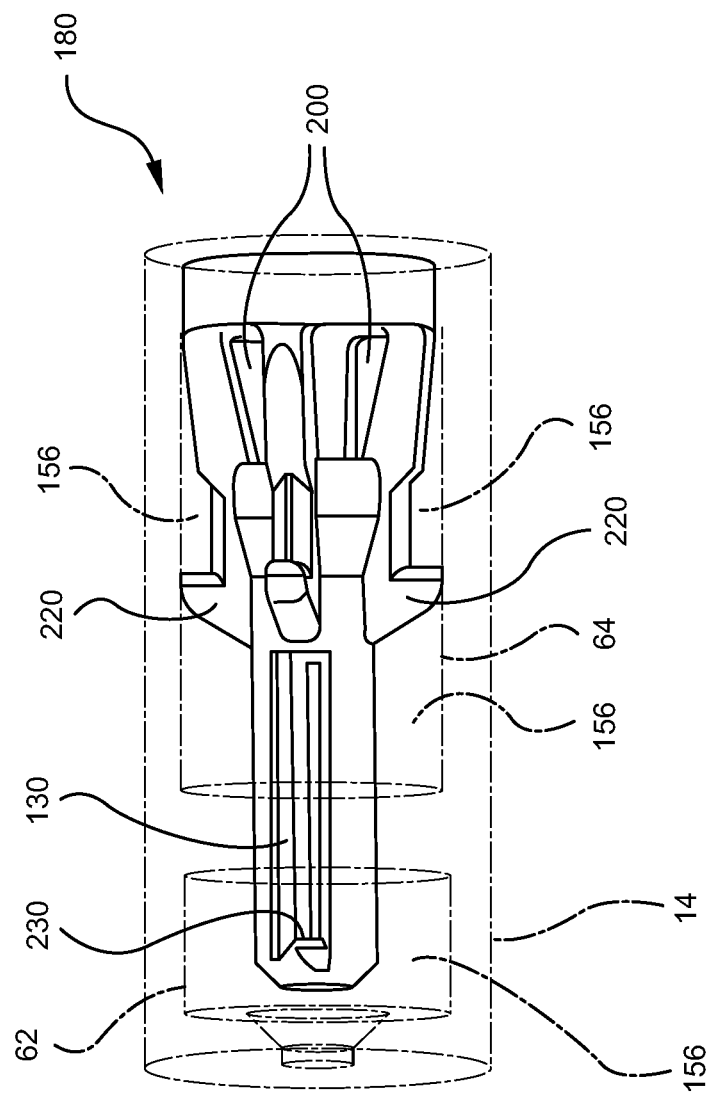
FIG. 6C is a side view of an embodiment of a septum activator disposed in an inner lumen of a catheter adapter in accordance with the present invention, following activation.

Referring now to FIG. 6C, an embodiment of a septum activator 180 is shown as positioned in the lumen of a catheter adapter 14 (shown in phantom). In some embodiments, septum activator 180 is configured to include various re-circulation features. For example, in some embodiments septum activator 180 includes various vents 200 configured to divert fluid from the fluid pathway 170 into the dead zones 156. Thus, as fluid flows into and through the septum activator 180, the fluid within the septum activator 180 passes through the vents 200 and into the dead zones 156 between the outer surface of the activator 180 and the inner wall surface of the catheter adapter 14. The diverted fluid intermixes with the fluid in the dead zones 156 to flush fluid from the dead zones 156 and thus prevent stagnation and/or overconcentration, as previously discussed.

In some embodiments, septum activator 180 is further modified to include flushing fins 220. Flushing fins 220 generally comprise perpendicular extension of the outer surface of the activator 180 that extend into the dead zones 156 between the activator 180 and the inner wall surface of the catheter adapter 14. The flushing fins 220 are provided to divert and redirect fluid within the fluid pathway 170 into the dead zones 156. As such, fluid within the dead zones 156 is intermixed with fluid in the fluid pathway 170 to prevent stagnation and/or overconcentration of fluid within the catheter adapter 14.

Finally, in some embodiments the flow diversion channel 130 is modified to include a flow deflector 230. The flow deflector 230 comprises a beveled, distal surface of the flow diversion channel 130 positioned to divert fluid within the fluid pathway 170 into the dead zones 156 of the forward fluid chamber 62. Thus, as fluid 146 flows through the septum activator 180, a portion of the fluid is diverted through the flow diversion channel 130 and into the dead zone 156 via the flow deflector 230, as shown in FIG. 6D.

Figure 6D:
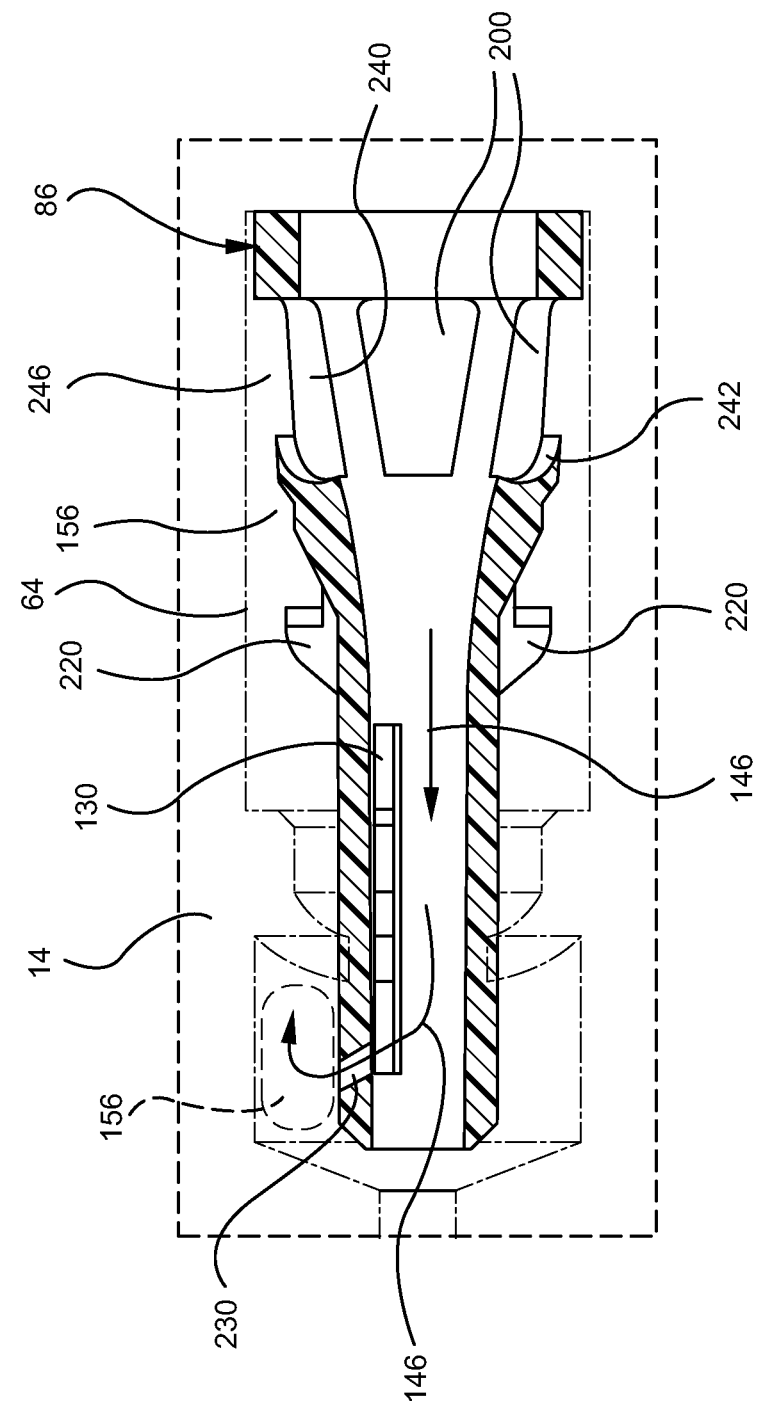
FIG. 6D is a side view of an embodiment of a septum activator disposed in an inner lumen of a catheter adapter in accordance with the present invention, demonstrating fluid flow through the catheter adapter.

With continued reference to FIG. 6D, a cross-sectioned septum activator 180 positioned within a cross-sectioned catheter adapter 14. As previously discussed, recirculation features may be added to both the proximal 86 and distal 186 ends of the septum activator 180. In some embodiments, the proximal end 86 of the septum activator 180 is modified to include curved window features 240 that redirect the flow of a fluid 246 into the dead zones 156 of the rearward fluid chamber 64. Thus, the curved surface 242 of the window feature 240 alone and/or in combination with the other recirculation features promotes intermixing of the fluid within the dead zones 156 to prevent stagnation and overconcentration of fluids within the catheter adapter 14.

In some embodiments, the recirculation features are positioned in a symmetrical configuration to induce best flushing. In other embodiments, the recirculation features are positioned in an asymmetrical configuration to induce best flushing. Finally, in some embodiments the recirculation features are used in combination with additional diffusing, circulating and recirculating features of the septum activator 180 to aid the fluid flushing capability of the septum activator 180. In light of the foregoing disclosure, additional surfaces of the septum activator 180 may be modified to increase or decrease flow efficiency, mixing and flushing of fluids within the septum activator 180, as desired.

Referring now to FIG. 7, a cross-sectional view of the assembled catheter assembly 101 is shown prior to activation of the septum 50 via the septum activator 80. Prior to activation, the septum activator 80 is entirely positioned within the rearward fluid chamber 64 of the catheter adapter 14. Additionally, the retention springs 110 are engaged within the retention groove 68 and positioned near the proximal end of the retention groove 68. The contact surface 140 of the septum activator 80 is positioned near the opening 26 of the catheter adapter 14, such that a proximal opening 142 of the septum activator 80 is in a plane generally parallel to the plane of the catheter adapter opening 26. Finally, the outwardly biased retention springs 110 bind on the surface of the groove 68 thereby maintaining the inactivated position of the septum activator 80 within the catheter adapter 14.

Referring now to FIG. 8, a cross-sectional view of the catheter assembly 101 is shown following activation of the septum 50 via the septum activator 80. Upon insertion of the coupler 42 into the proximal opening 26 of the catheter adapter 14, the probe portion 46 of the coupler 42 contacts the contact surface 140 of the septum activator 80. The septum activator 80 is advanced in a distal direction 390 as the coupler 42 is further inserted into the proximal opening 26 of the catheter adapter 14. As the coupler 42 is advanced further into the proximal opening 26, the probing surface 90 of the septum activator 80 passes through the barrier surface 52 of septum 50. As such, the probing surface 90 of the septum activator 80 is positioned within the forward chamber 62 providing a fluid pathway through the septum 50.

In some embodiments, the catheter assembly 101 is configured to permit the septum activator 80 to return to a position entirely within the rearward chamber 64 following removal of the coupler 42 from the catheter adapter 14. Thus, when the coupler 46 is removed or detached from the catheter assembly 101, the fluid pathway through the septum 50 is reclosed. In some embodiments, the retention spring 110 is configured to flex inwardly upon contact between the contact surface 140 of the septum activator 80 and the probe 46 of the coupler 42. When the retention spring 110 flexes inwardly, the probing surface 90 of the septum activator 80 is temporarily advanced in a distal direction 390 to bias open the slits 66 and 56, or the leak orifice 58. When contact between the probe 46 and the contact surface 140 ceases, the retention spring 110 returns to its relaxed position. The relaxed position withdraws the probing surface 90 of the septum activator 80 from the barrier surface 52 thereby permitting closure of the slits 66 and 56.

Figure 9:
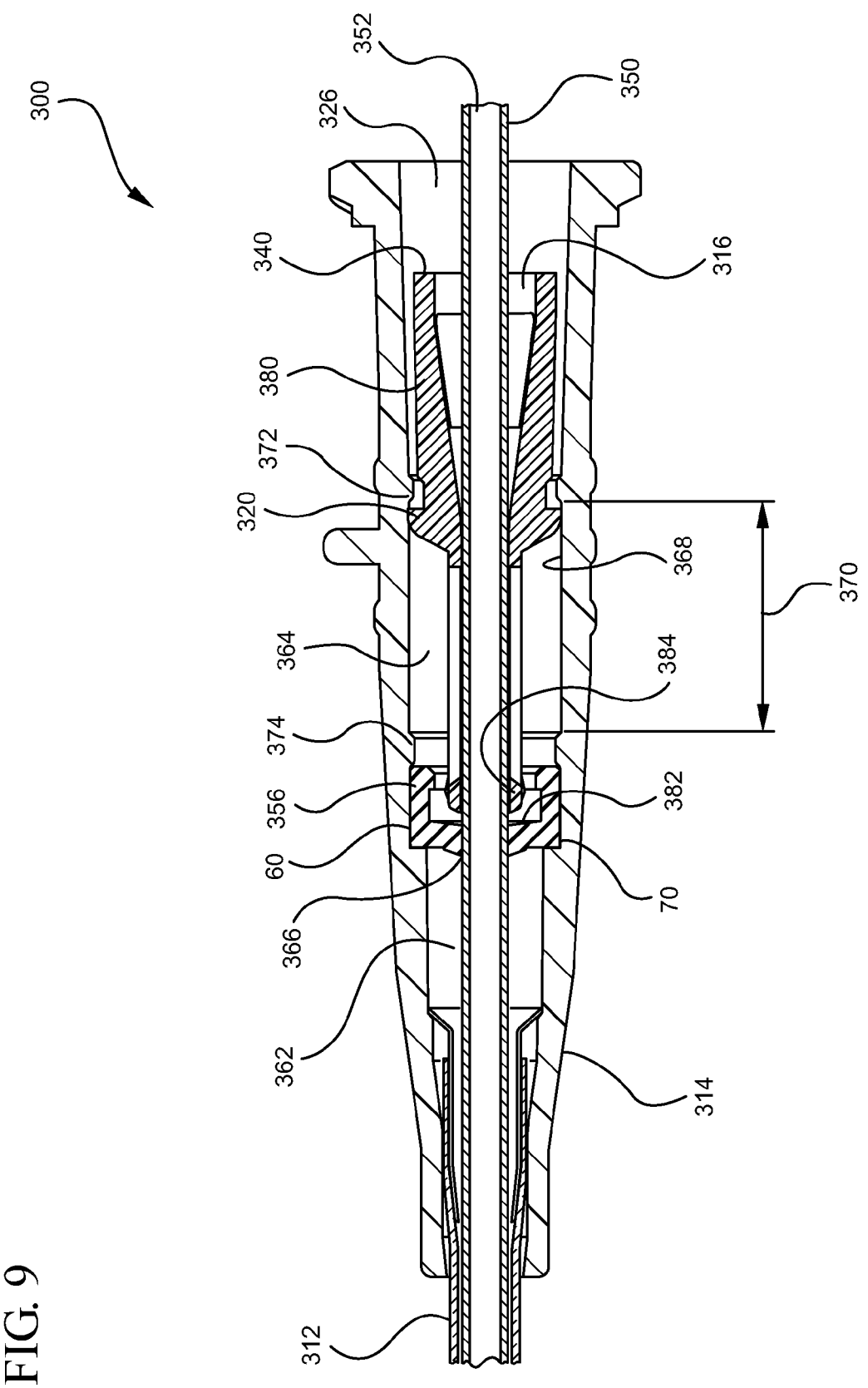
FIG. 9 is a cross-sectioned view of an assembled over-the-needle catheter assembly in accordance with the present invention, prior to activation.

Referring now to FIG. 9, a cross-sectional view of a catheter assembly 300 is shown incorporating an introducer needle 350. The proximal end 352 of the needle 350 may be coupled to a needle hub (not shown) or an insertion assembly (not shown) to facilitate a user in holding and manipulating the needle 350 during catheterization. For purposes of clarity in the present illustration the remainder of the needle assembly has been removed.

Prior to activation, septum activator 380 is entirely positioned within the rearward chamber 364 of catheter adapter 314. A pathway is provided through the inner lumen 316 of the activator 380 so as to allow passage of introducer needle 350. A middle portion of the needle 350 passes through septum 356 and continues through the forward chamber 362 and into the flexible catheter 312. A tip portion (not shown) of the needle 350 extends beyond a tip portion (not shown) of the catheter 312 such that the needle tip is available to gain access to the vasculature of a patient.

The slit 366 of septum 356 is biased open by introducer needle 350. In some embodiments, a seal is formed between the outer surface of the needle 350 and the slit 366. Thus, fluid and air flow are prevented from bypassing the septum by way of the interface between the needle 350 and the slit 366. In some embodiments, a channel or pathway is provided between the slit 366 and the needle 350 to permit controlled leakage or flow between these two components.

In other embodiments, a lubricant such as a non-wetting lubricant is applied to the interface between the needle 350 and the slit 366 to further eliminate possible leakage of fluid and/or air. A non-wetting lubricant may also be beneficial to prevent tearing or other damage to the slit that may occur when the needle is removed from the catheter assembly following catheterization. A non-wetting lubricant may also facilitate proper realignment of the slit 366 halves following removal of the needle 350. Non-limiting examples of a non-wetting lubricant include known Teflon based non-wetting materials such as Endura, from Endura Coating Co.; A20, E-20, 1000-S20, FEP Green, PTFE and X-40 from Tiodize; Cammie 2000 from AE Yale; 21845 from Ladd Research; MS 122-22, MS 122DF, MS-143DF, MS-122V MS-122VM, MS143V, MS-136W, MS-145W, U0316A2, U0316B2, MS-123, MS-125, MS-322 and MS-324 from Miller-Stepheson; and 633T2 from Otto Bock can also be used. Various non-Teflon based non-wetting lubricant type materials include Dylyn, from ART; Nyebar, Diamonex, NiLAD, TIDLN, Kiss-Cote, Titanium oxide; Fluocad Fluorochemical Coating FC-722, from 3M; Permacote from Dupont; Plasma Tech 1633 from Plasma Tech, Inc.; and silicone sprays.

In some embodiments, distal end 384 of the septum activator 380 is elongated such that contact surface 340 is positioned closer to proximal opening 326 of the catheter adapter 314. Accordingly, a coupler having a shortened probe portion (not shown) may sufficiently contact the contact surface 340 to advance the distal end 384 through the septum 356. In other embodiments, the distal end 384 of the septum activator 380 is configured to include an inner diameter of substantially the same size and the outer diameter of the introducer needle 350. As such the inner diameter of the distal end 384 is configured to allow passage of the needle 350 while maintaining minimal tolerance 382 between the outer surface of the needle 350 and the inner surface of the septum activator 380 distal end 384. This minimal tolerance 382 provides a seal thereby preventing leakage or flow of blood between the needle 350 and the septum activator 380 while withdrawing the needle 350 from the catheter assembly 300.

In some embodiments, a translating groove 368 is provided within the rearward chamber 364. The translating groove 368 generally comprises an annular recess having a determined length 370. Translating groove 368 is further configured to receive flushing fins 320 such that the flushing fins 320 are retained within the groove 368. Thus, length 370 represents the maximum lateral distance which septum activator 380 is permitted to travel within the rearward chamber 364. In some embodiments, a proximal end of groove 368 is defined by an annular ridge 372. In other embodiments, a distal end of groove 368 is defined by a second annular ridge 374. Still, in other embodiments the second annular ridge 374 forms a proximal end of septum channel 60.

Figure 10:
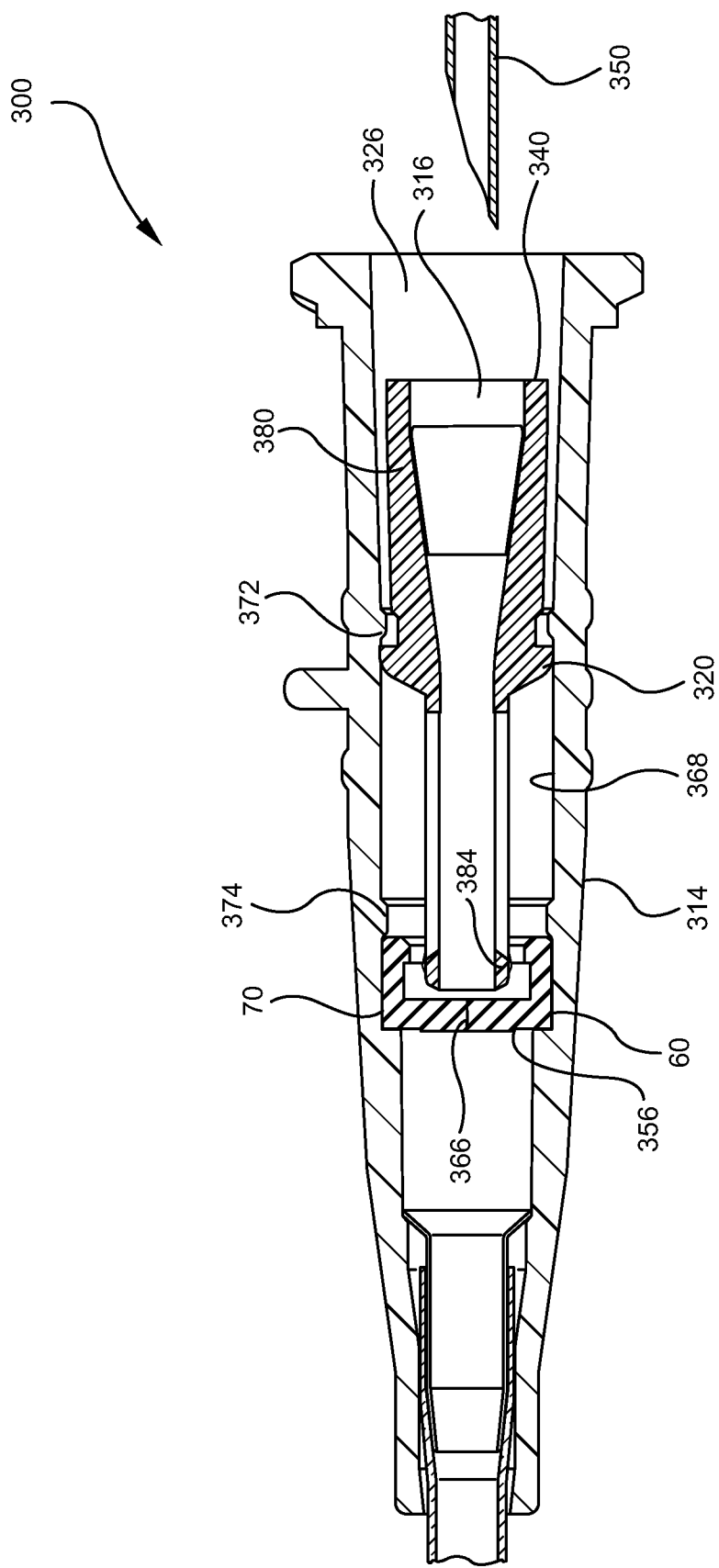
FIG. 10 is a cross-sectioned view of an assembled over-the-needle catheter assembly in accordance with a representative embodiment of the present invention, following removal of the introducer needle.

Referring now to FIG. 10, a cross-sectional view of catheter assembly 300 is shown following removal of introducer needle 350. Upon removal of introducer needle 350, slit 366 of septum 356 is no longer biased open and therefore recloses and seals to prevent flow of fluids and/or air via the slit 366. As previously discussed, in some embodiments slit 366 includes a leak orifice (not shown) to permit controlled flow between the forward and rearward chambers 362 and 364. In other embodiments, a plurality of ventilation channels 70 are provided between the outer surface of the septum 356 and the septum channel 60.

Figure 11A:
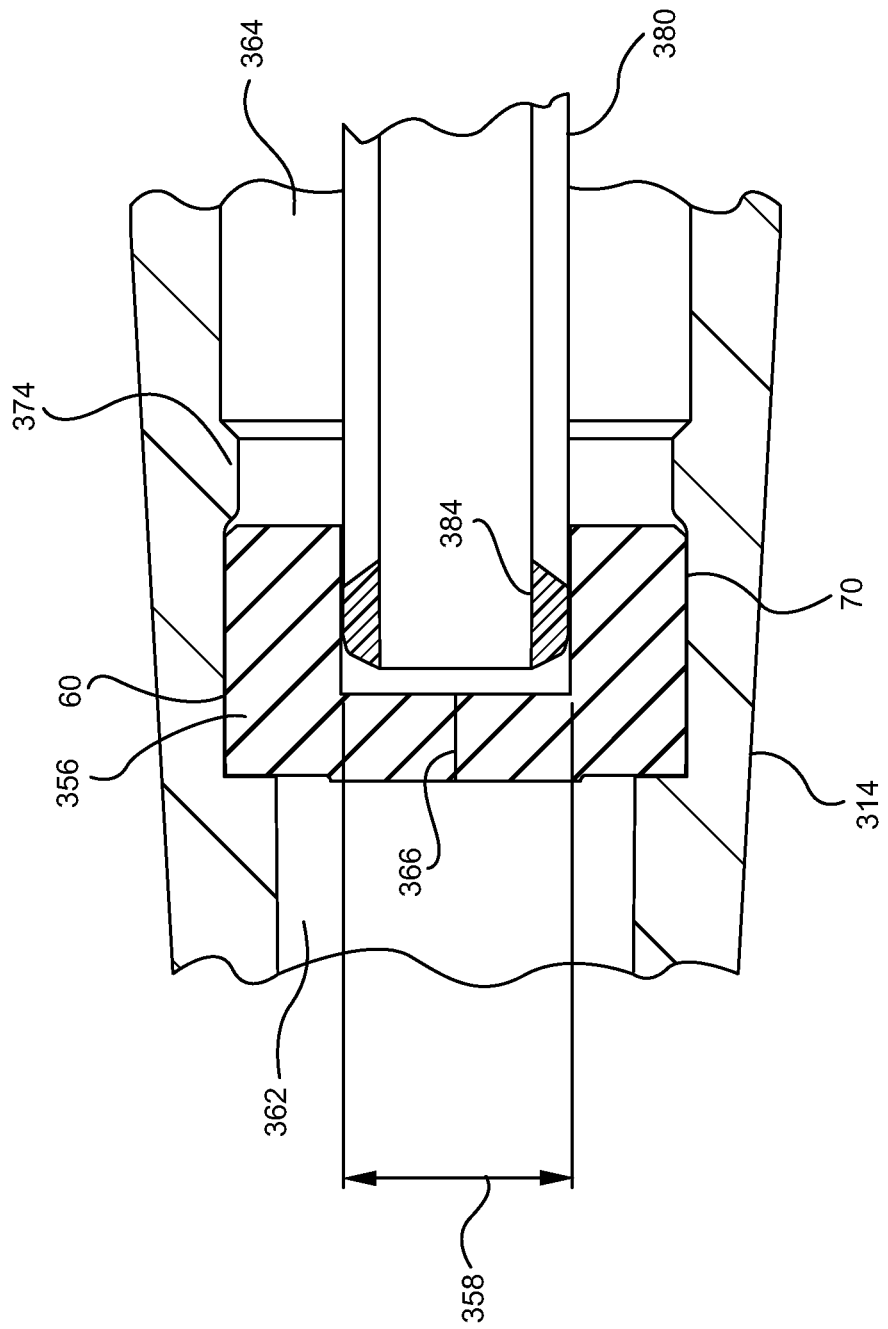
FIGS. 11A through 11D are cross-sectioned views of septum having various features and configuration in accordance with representative embodiments of the present invention.
Figure 11B:
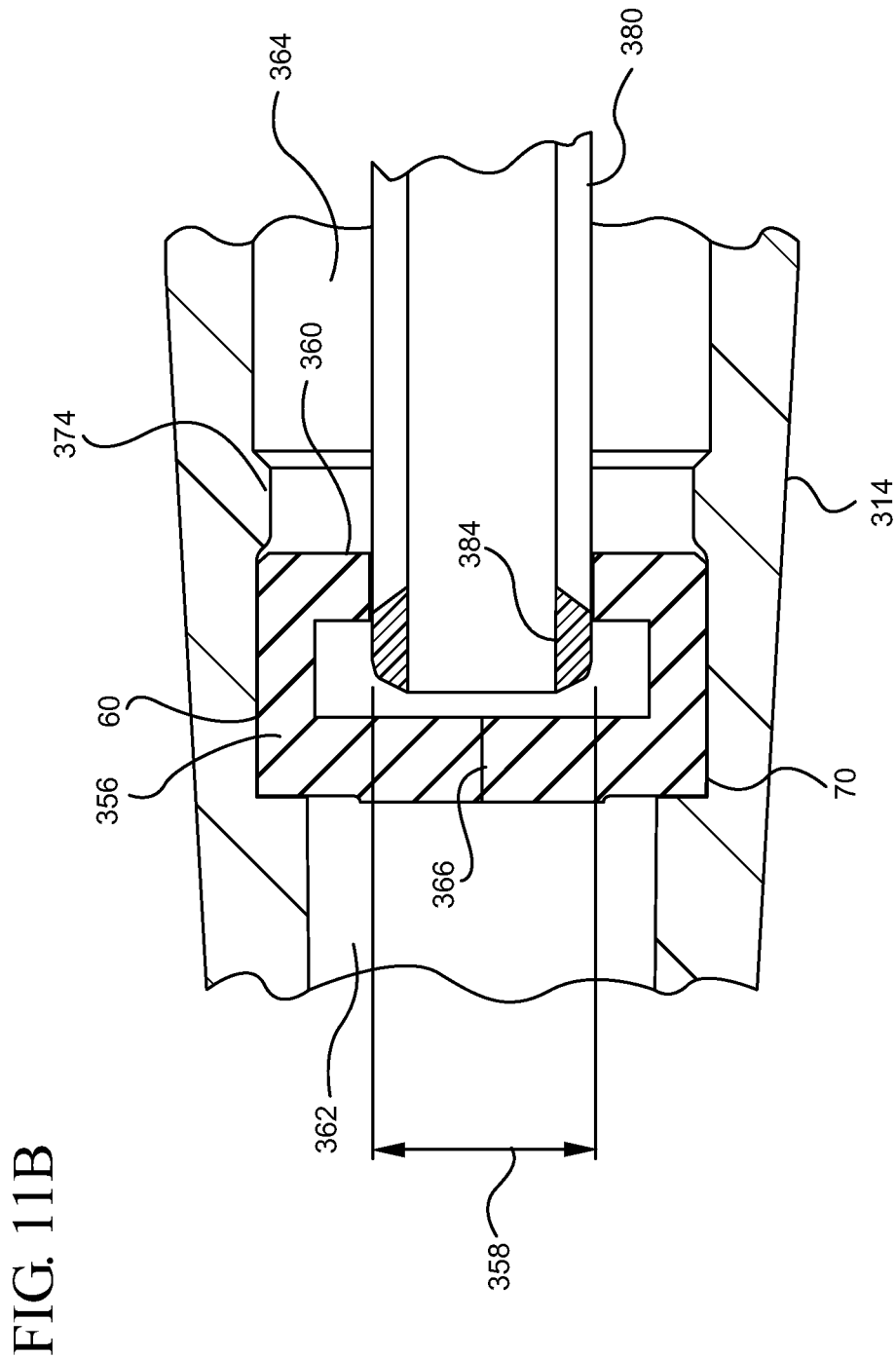

Referring now to FIGS. 11A through 11D, septum 356 may include various configurations and features to stabilize distal end 384 of the septum activator 380. For example, in some embodiments septum 356 is configured to include an inner diameter 358 sized substantially equal to the outer diameter of the distal end 384 of septum activator 380, as shown in FIG. 11A. In other embodiments, septum 356 is configured to have an interior annular ridge or protrusion 360 having an inner diameter 358 sized substantially equal to the outer diameter of distal end 384, as shown in FIG. 11B. Thus, in both of these embodiments distal end 384 is radially supported by septum 356.

Figure 11C:
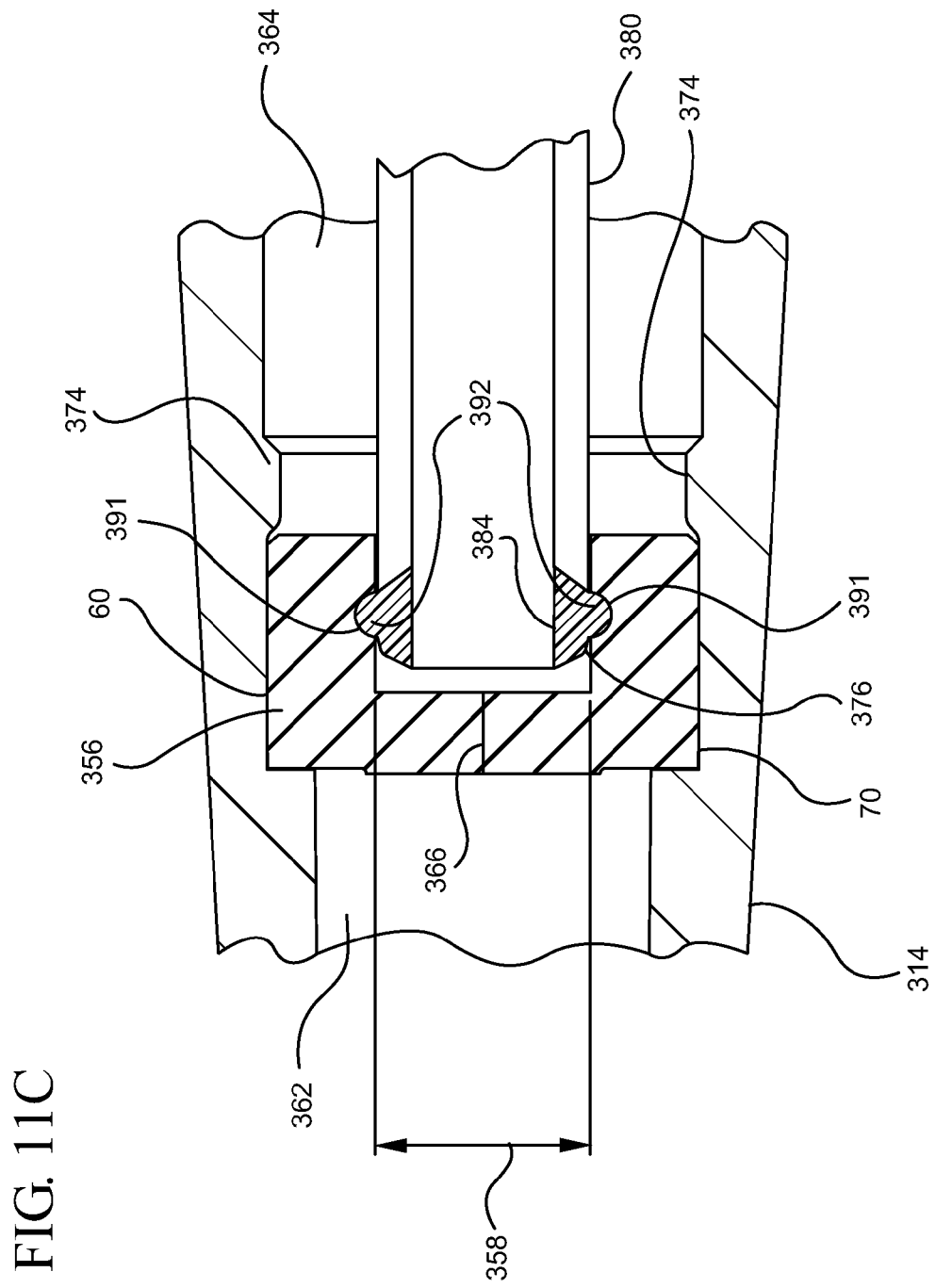

With reference to FIG. 11C, in some embodiments an interior surface 376 of septum 356 is modified to include one or more reliefs 391. In some embodiments, relief 391 comprises a concave annular recess configured to receive a positive feature 392 comprising a portion of distal end 384 of the septum activator 380. In other embodiments, relief 391 comprises a singular indent sized and configured to receive feature 392 of the septum activator 380. Still, in other embodiments relief 391 comprises a positive feature and feature 392 comprises a negative or recessed feature (not shown). Thus, in some embodiments the interaction between relief 391 and feature 392 provides both radial support and axial retention of the septum activator 380 within the catheter adapter 314. This configuration may eliminate the need for additional retention features, such as clips and retention grooves.

Figure 11D:
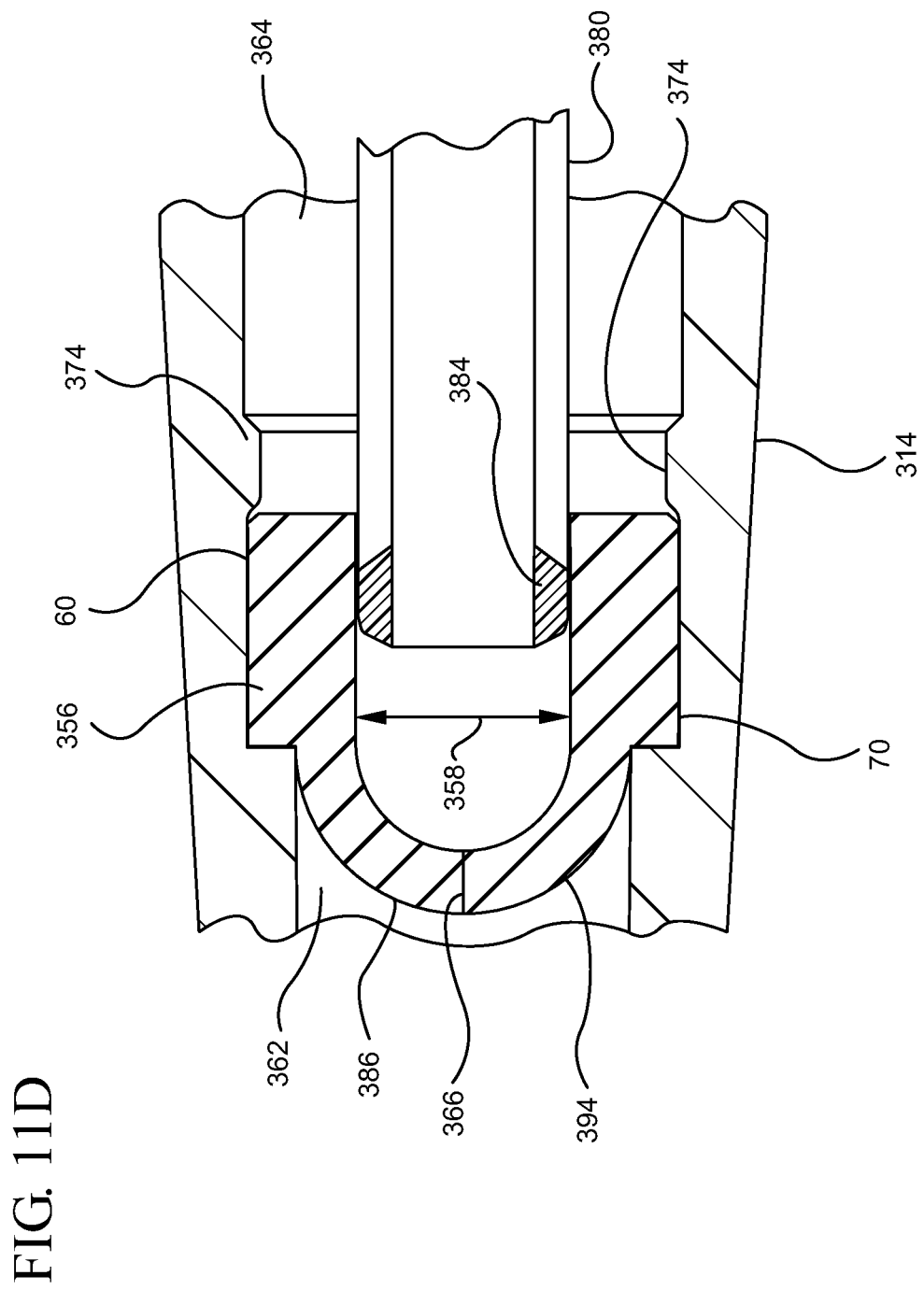

Referring now to FIG. 11D, septum 356 includes a domed profile 394 to counteract pressure applied to the distal side 386 of the septum 356 following removal of introducer needle 350. The domed profile 394 provides additional strength to the distal side 386 of the septum 356 thereby increasing the fluid pressure required to defeat the septum 356. In some embodiments, as the blood reaches the septum 356 the domed profile 394 assists the septum 356 in closing due to the pressure from the blood flow within the forward chamber 362. In other embodiments, septum 356 comprises a generally flat profile, as shown in FIGS. 5A, 5B and 7 through 11C or may include a combination of flat and curved surfaces (not shown).

Figure 12:
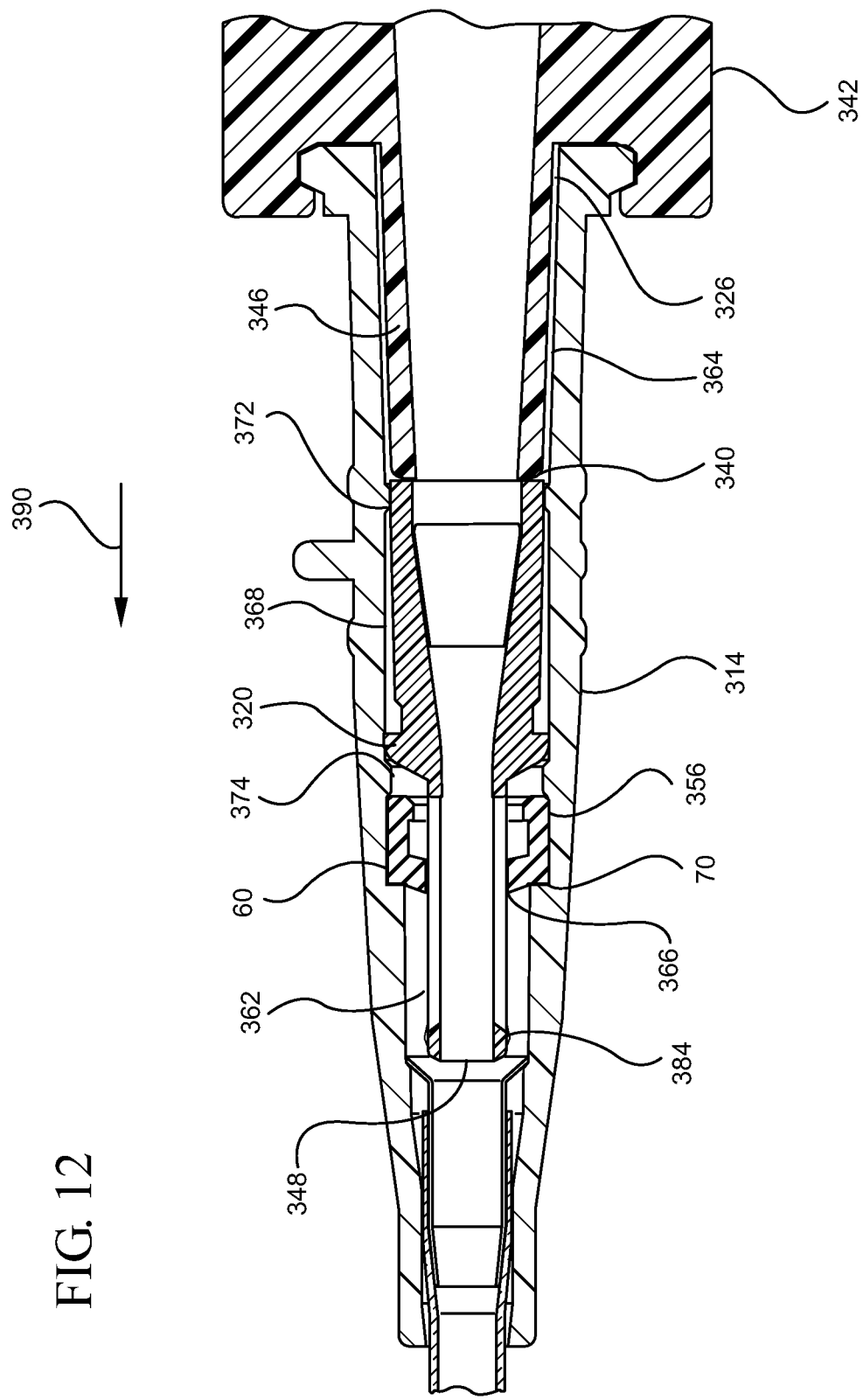
FIG. 12 is a cross-sectioned view of an assembled over-the-needle catheter assembly in accordance with a representative embodiment of the present invention, following activation.

Referring now to FIG. 12, a cross-sectional view of catheter assembly 300 is shown following activation of septum 356 via septum activator 380. Upon insertion of a coupler 342 into the proximal opening 326 of the catheter adapter 314, the probe portion 346 of the coupler 342 contacts the contact surface 340 of septum activator 380. Septum activator 380 is accordingly advanced in a distal direction 390 as the coupler 342 is further inserted into proximal opening 326 thereby causing flushing fins 320 to translate within translating groove 368. As coupler 342 is advanced further into the proximal opening 326, probing surface 348 of the septum activator 380 passes through the slit 366 of septum 356. As such, the probing surface 348 of the septum activator 380 is positioned within the forward chamber 362 providing a fluid pathway through the septum 356.

Referring now to FIGS. 13 through 20, a number of valves in accordance with some embodiments are shown which aim to further eliminate or reduce areas of low or no fluid flow occurring within a vascular access device containing a valve mechanism comprising a septum and septum activator or pusher.

Figure 13:
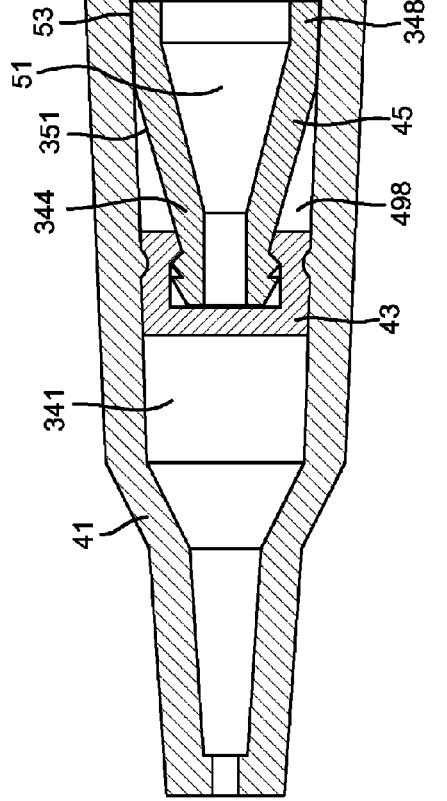
FIG. 13 is a cross-sectioned view of a catheter body having a flow control valve mechanism and a septum activator in accordance with a representative embodiment of the present invention, prior to activation.
Figure 14:
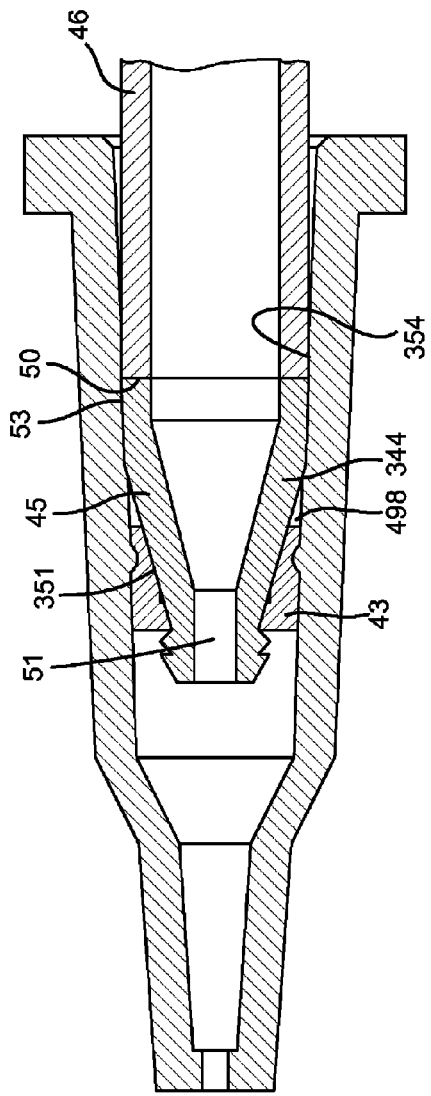
FIG. 14 is a cross-sectioned view of a catheter body having a flow control valve mechanism and a septum activator in accordance with a representative embodiment of the present invention, following activation.

FIGS. 13 and 14 show an embodiment of the invention in which a sleeve 45 is used to prevent fluid from flowing into any interstitial spaces which are low or no flow fluid areas.

FIG. 13 shows a septum 43 which forms a fluidic seal in the lumen 341 of catheter body 41 after removal of the needle, with septum activator or pusher 344 in the proximal position. Sleeve 45 is attached around pusher 344 to form a fluid seal between an outer periphery 53 of proximal portion 348 of pusher 344 and inner surface 354 of lumen 341. Thus, no fluid can flow between the proximal end of pusher 344 and the inner surface 354 of lumen 341 into the interstitial space 498. FIG. 14 shows pusher 344 in the distal position in which fluid can only flow via the lumen 51 of pusher 344. Sleeve 45 still maintains a fluidic seal between outer periphery 53 of pusher 344 and inner surface 54 of lumen 341. Thus, no fluid can flow into the interstitial spaces 498. In addition, the tapered outer surface 351 of the distal portion of sleeve 45 reduces the size of the interstitial space 498 when pusher 344 is in the distal position. Sleeve 45 is made from a softer elastomeric material, such as liquid silicone rubber for example, and is attached to pusher 344 through suitable molding procedures, such as insert molding, injection molding, and other molding techniques or a combination of molding techniques.

Figure 15:
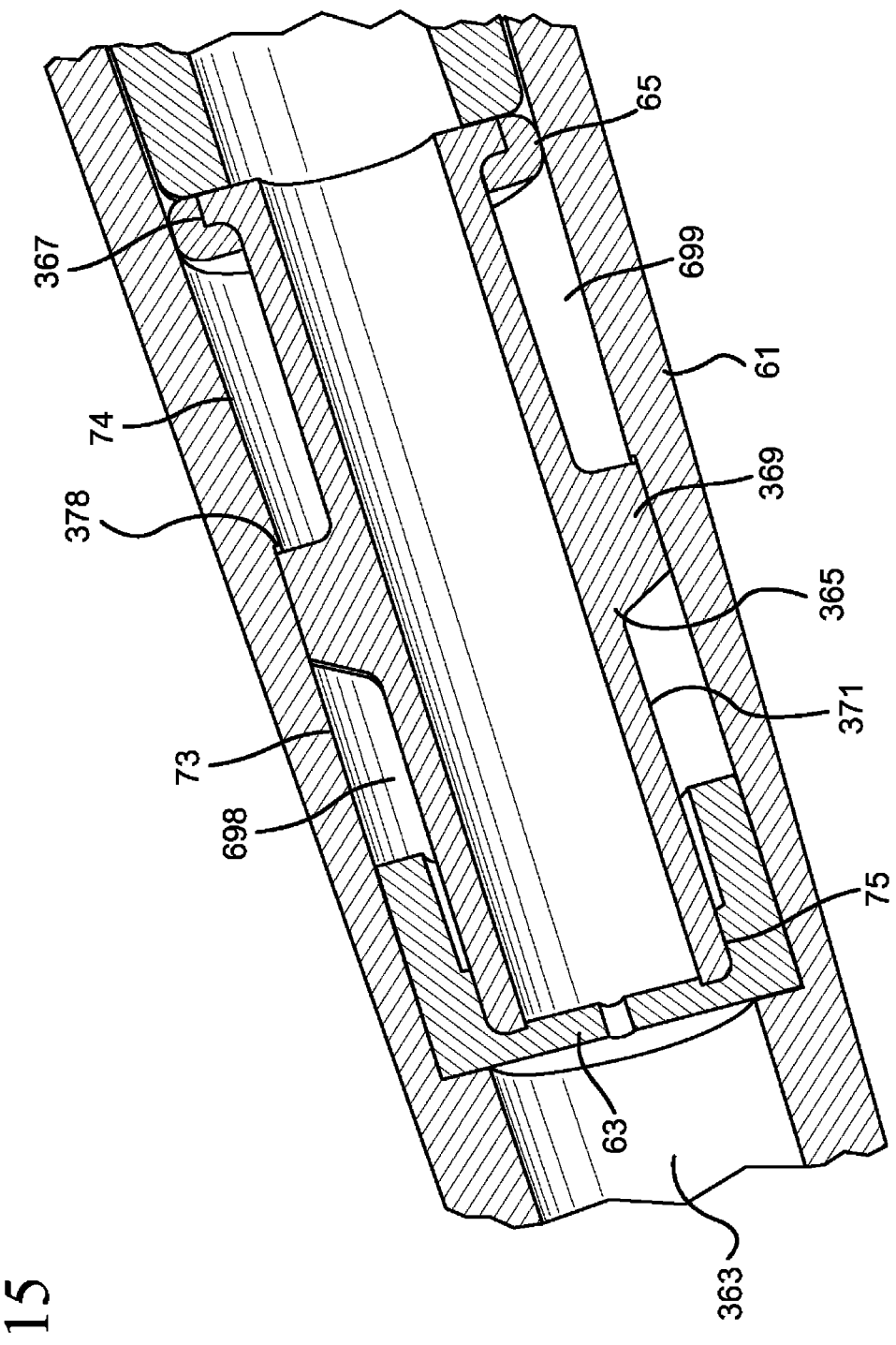
FIG. 15 is a cross-sectioned view of a catheter body having a flow control valve mechanism and septum activator in accordance with a representative embodiment of the present invention, prior to activation.
Figure 16:
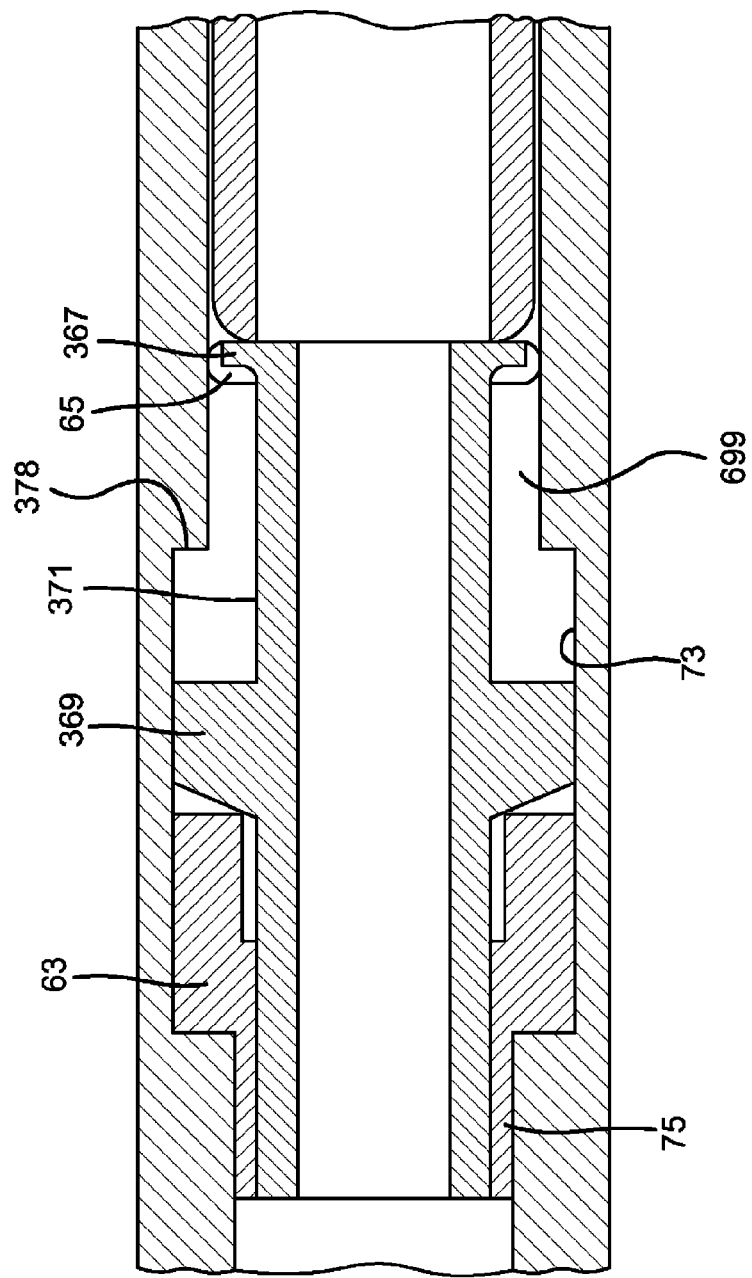
FIG. 16 is a cross-sectioned view of a catheter body having a flow control valve mechanism according to the representative embodiment shown in FIG. 15, following activation.

FIGS. 15 and 16 show another embodiment of the invention having valve mechanism which uses a seal at the proximal end 65 and distal end 75 of a tubular septum activator 365, to prevent fluid from flowing into interstitial spaces 698 and 699 between activator 365 and the inner surface 74 of the lumen 363 of the catheter body 61. Distal seal 75 is incorporated into septum 63 to prevent any fluid flowing between the distal end of activator 365 and the proximal surface of septum 63 when pusher is in the proximal position as shown in FIG. 15 or the distal position as shown in FIG. 16. Proximal seal 65 is a continuous torus or toroidal-shaped band around the outer circumference of the proximal end of activator 365 which forms a fluid seal with the inner surface 74 of the lumen 363 of the catheter body 61 in both the proximal and distal activator positions. The proximal seal 65 is made from a softer elastomeric material, such as liquid silicone rubber for example and is over-molded onto activator 365 and retained in position by lip 367 on the outer surface of the proximal end of activator 365. Activator 365 has a number of fins 369 extending from and evenly distributed around the circumference of the outer surface 371. These fins 369 are sufficiently long to contact a portion 73 of the inner surface 74 of lumen 363 and are used to limit the movement of activator 365 along the catheter body by contact with the septum 63 in the distal direction and contact with indent or step 378 of the inner surface 74 in the proximal direction.

FIGS. 17 through 20 show some embodiments having valve mechanisms which are configured to exclude small confined interstitial spaces, thereby eliminating areas of no to low fluid flow.

Figure 17:
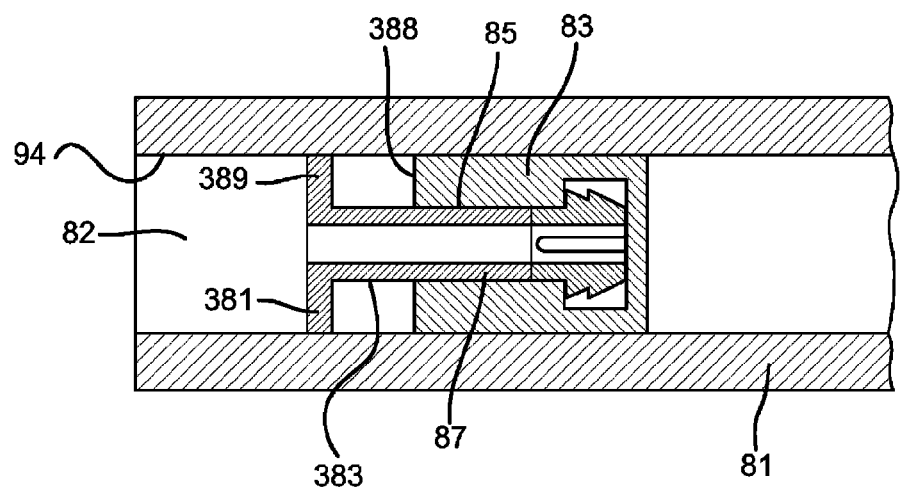
FIG. 17 is a cross-sectioned view of a catheter body having a flow control valve mechanism and septum activator in accordance with a representative embodiment of the present invention, prior to activation.
Figure 18:
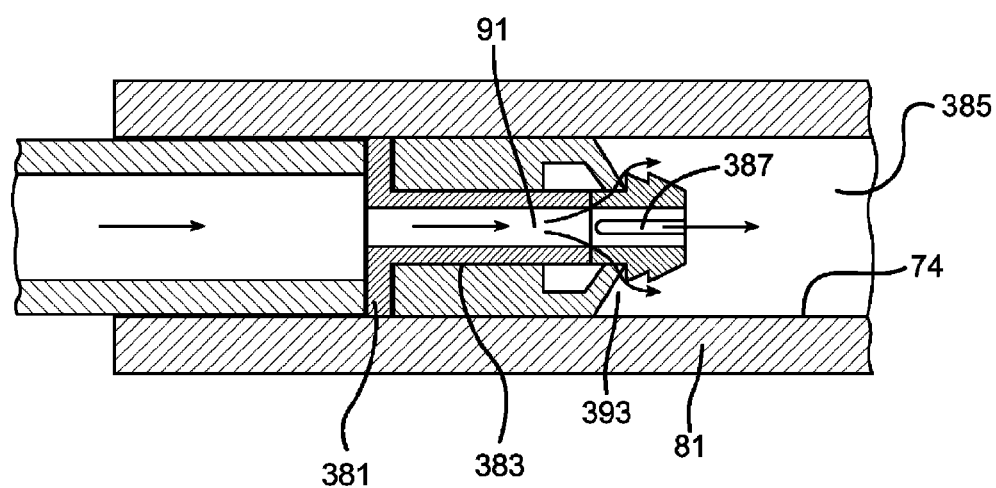
FIG. 18 is a cross-sectioned view of a catheter body having a flow control valve mechanism according to the representative embodiment shown in FIG. 17, following activation.

FIGS. 17 and 18 show an embodiment in which the septum 83 encases the majority of activator 383. Activator 383 includes a head section, tubular section and a plunger. Plunger 381 which has a diameter at least equal to that of lumen 385 of the catheter body 81 such that no fluid can pass between the inner surface 94 and plunger 80 is located at the proximal end of activator 383. Septum 83 has an external diameter at least equal to that of lumen 82 along its entire length such that no interstitial space is present between septum 83 and inner surface 94 of lumen 385. In addition, septum 83 has a lumen 85, the internal diameter of which is equal to the external diameter of tubular section 87 of activator 383 thereby forming an additional fluid seal along the length of tubular section 87. Furthermore, the relative lengths of activator 383 and septum 83 are such that the distal face 389 of plunger 381 is in intimate contact with the proximal end 388 of septum 83 when activator 383 is in the distal position, as shown in FIG. 18. Thus, there is no interstitial space between plunger 381 and septum 83. The head section is located at the distal end of activator 383 and includes longitudinal slots 387 in the side wall of lumen 91 in order to allow fluid flow to diverge out of lumen 91 of activator 383 and reduce the possibility of a no or low flow area 393 around the distal face of septum 83 at the inner surface 74.

Figure 19:
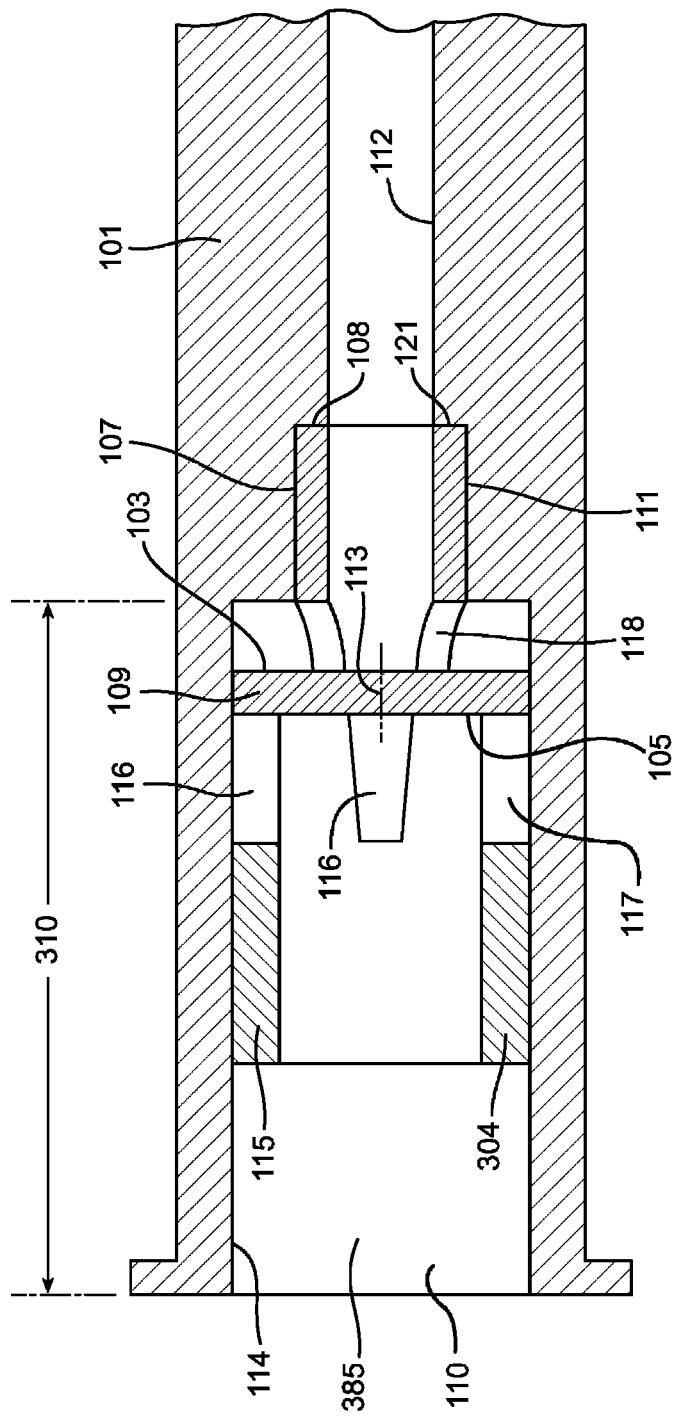
FIG. 19 is a cross-sectioned view of a catheter body having a flow control valve mechanism and septum activator in accordance with a representative embodiment of the present invention, prior to activation.
Figure 20:
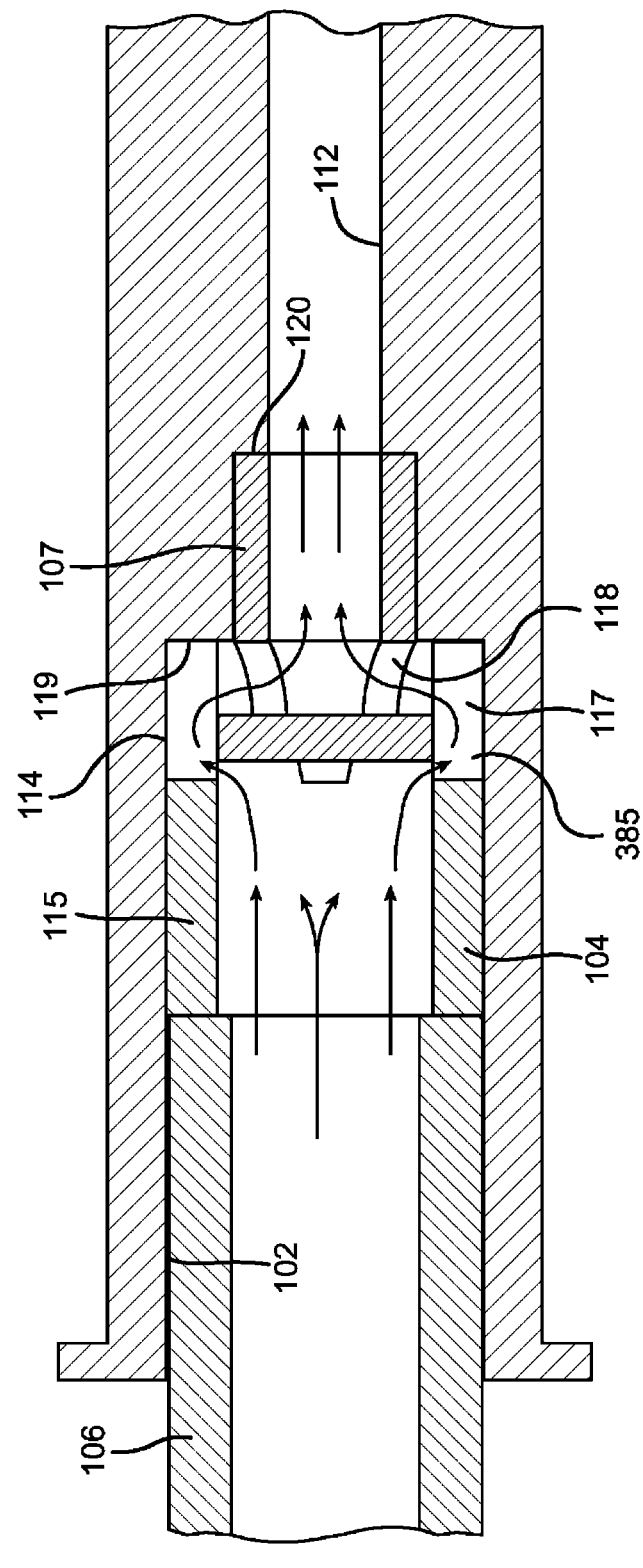
FIG. 20 is a cross-sectioned view of a catheter body having a flow control valve mechanism according to the representative embodiment shown in FIG. 19, following activation.

FIGS. 19 and 20 show a further embodiment of a valve mechanism in which a septum 103 includes a tubular section 107 having a distal end 108 and a membrane section 109 having a proximal planar surface located at the proximal end 105. The tubular section 107 of septum 103 is substantially disposed within septum housing 111 and is prevented from distal movement by shoulder or annular recess 121 formed in surface of lumen 385. A fluidic seal is formed between the periphery of membrane section 109 and inner surface 114 of the proximal section 110 of lumen 385 to prevent fluid leakage past septum 103 when the valve is closed. In some embodiments, septum 103 further includes a needle slit 113 or valve aperture located about the centre of membrane section 109, extending through membrane section 109, to facilitate penetration of septum 103 by introducer needle 5. A septum activator 304 is located in the proximal section of lumen 385 and includes a tubular portion 115. In some embodiments, tubular or sleeve portion 115 further includes a plurality of longitudinal slots or flow channels 116 in the side wall, distributed evenly around the circumference of tubular potion 115 and located at the distal or actuating end 117 such that a gap is formed between the actuating end 117 and membrane 109.

FIG. 19 shows septum activator 304 in the proximal position following removal of introducer needle 5. In particular, the actuating end 117 of septum activator 304 is positioned against the proximal planar surface of membrane section 109 of septum 103 to form an interface. The diameter of lumen 385 in proximal section 310 is approximately equal to the external diameter of connector 106 (e.g. a luer connector) of a vascular access device, septum activator 304 and membrane section 109, such that there are no interstitial spaces between the connector 106 (shown in FIG. 20), a contact end of septum activator 304 and membrane section 109. The inner surface 114 and proximal section 310 of the first lumen 385 are further sealed by membrane section 109.

Referring now to FIG. 20, septum activator 304 is shown in the distal position whereby connector 106 has repositioned septum activator 304 forward in a distal direction thereby causing actuating end 117 of septum activator 304 to deform membrane section 109. This deformation results in the formation of a fluid pathway whereby fluid bypasses membrane section 109 via slots 116, thereafter flowing between periphery of membrane section 109 and inner surface 114, and guided through opening 118 in the side wall of tubular portion 107. This divergent fluid path around the periphery of membrane section 109 causes a turbulent fluid flow which reduces the possibility of stagnation or a low flow area occurring near shoulder 119 in lumen 385. Fluid then continues to flow along the internal diameter of tubular portion 107 and into the distal section 112 of lumen 385.

Figure 21:
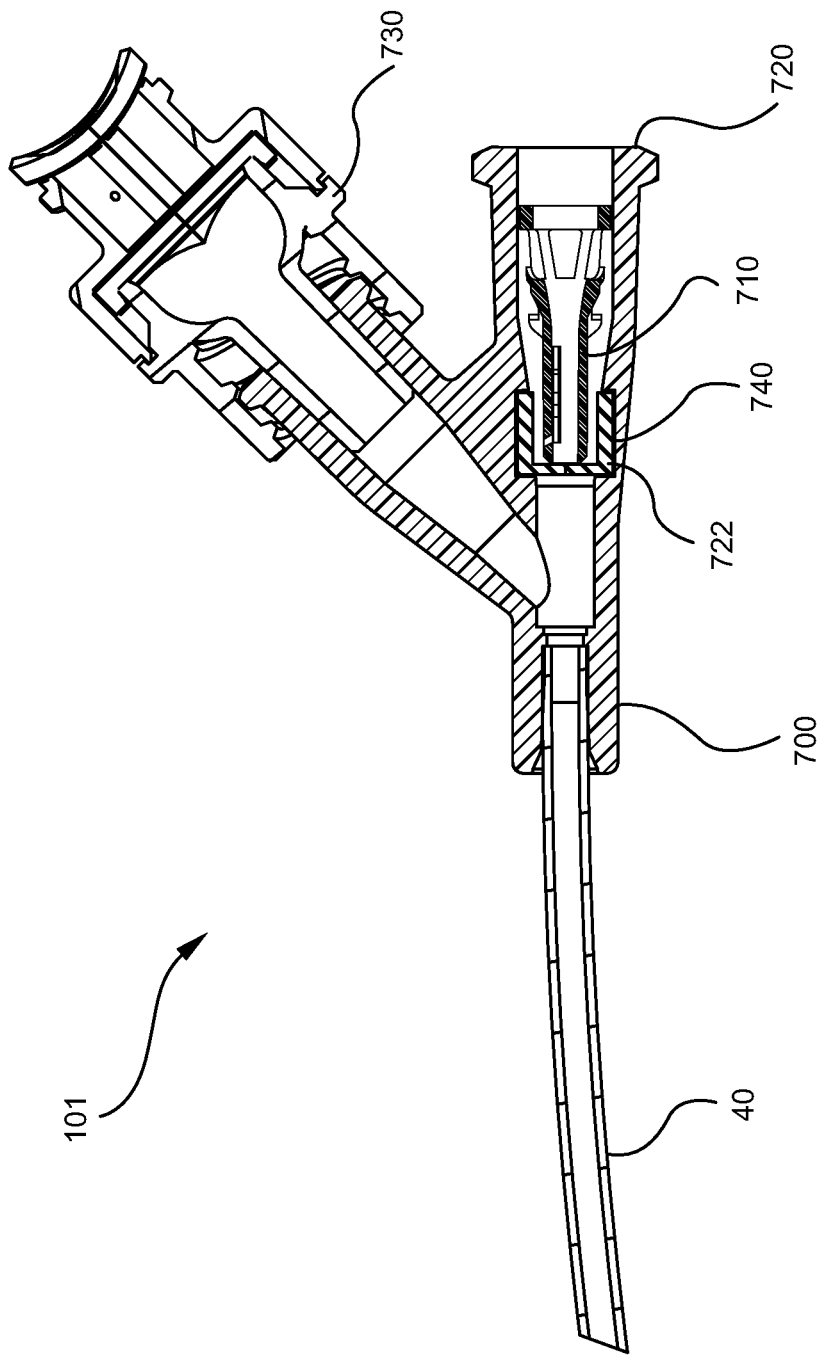
FIG. 21 is a cross-sectioned view of a vented blood control valve and y-port adapter having a flow control valve mechanism in accordance with a representative embodiment of the present invention, prior to activation.
Figure 22:
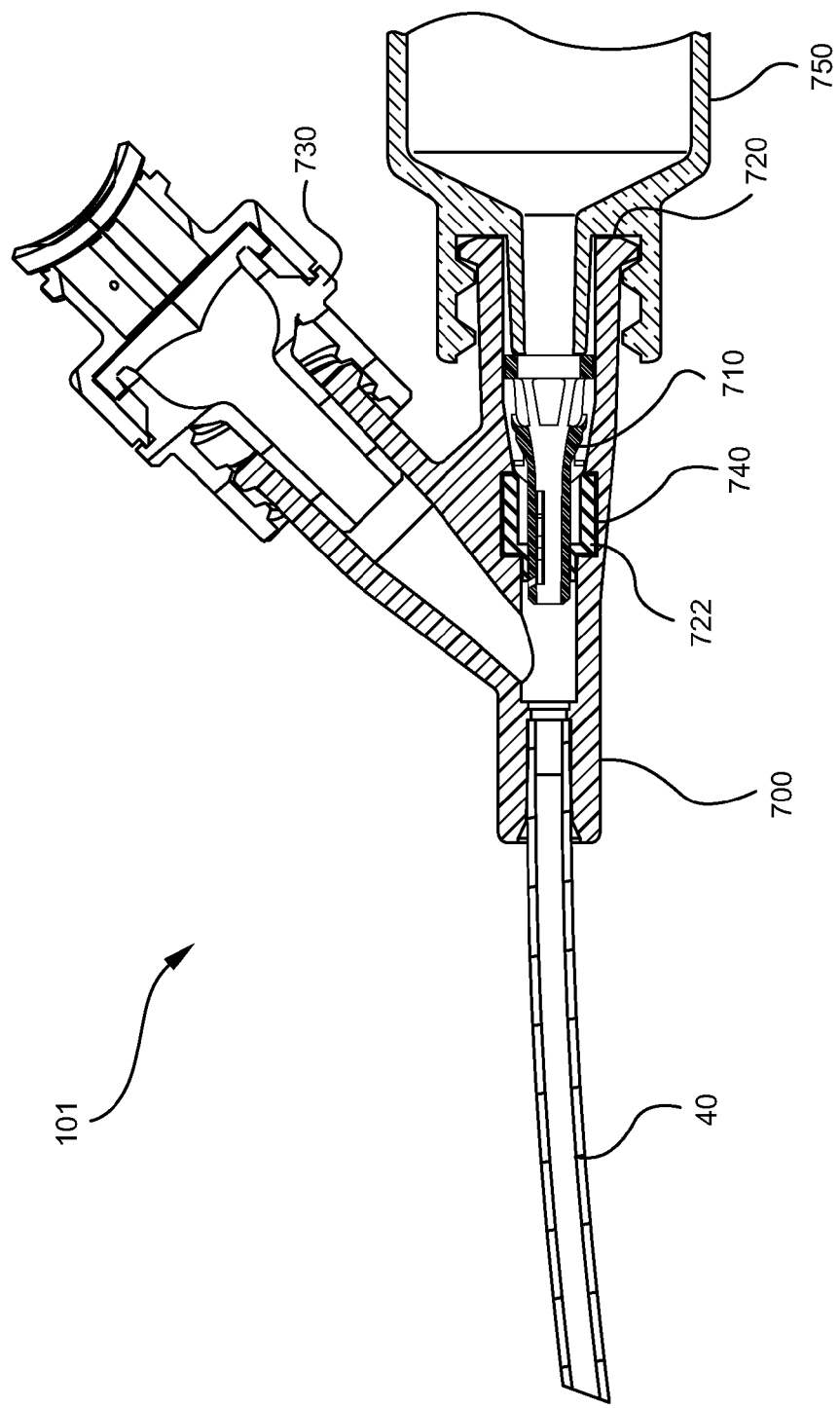
FIG. 22 is a cross-sectioned view of a vented blood control valve and y-port adapter having a flow control valve mechanism in accordance with a representative embodiment of the present invention, following activation.

Referring now to FIGS. 21 and 22, in some embodiments catheter assembly 101 further comprises an auxiliary y-port 700 configured to include a blood control valve 710 in accordance with any of the teachings of the present invention. Although control valve 710 is shown incorporated into an auxiliary y-port 700, the various blood control valves of the present invention may be incorporated into any single or multiple use blood control valve system that permits passage of air (i.e.: vents) but stop blood flow.

In some embodiments, a blood control valve 710 is positioned within the straight luer portion 720 of the closed IV catheter system 101, as shown. In other embodiments, a blood control valve 710 is positioned within the y-luer 730 portion of the closed IV catheter system 101. Still further, in some embodiments a blood control valve 710 is positioned within both the straight 720 and y-luer 730 portions of the IV catheter system 101 (not shown). In some embodiments, the blood control valve 710 comprises a septum 722 disposed within the y-port 700, wherein valve 710 further comprises a ventilation channel 740 interposed between the septum 722 and the y-port 700 to permit passage of at least one of air and blood at a desired rate of flow.

Initially, the valve system comes in the unactuated position, as shown in FIG. 21. The unactuated position allows venting of the closed system in channels 740 located between the luer adapter 720 and the valve septum 722. In some embodiments, channels 740 are sized to allow airflow, but prevent blood flow. The vented valve therefore replaces the need of including a vent plug to prime the IV line 40. During the catheterization process, blood is therefore permitted to flow into the IV line 40 until it reaches septum 722, at which point the blood flow ceases. The clinician may then simply attach any connecting device 750 to allow infusion, blood draw, or fluid delivery, as shown in FIG. 22.

In some embodiments, the clinician simply adds a cap or cover (not shown) to the luer port 720 thereby preventing contamination until later use. Upon connection of the connecting device 750, the septum activator of valve 710 is advanced through septum 722 thereby opening valve 710 to allow free flow of fluid and normal infusion therapy practices. Unlike other valve systems, long term compression set of the cannula and valve integration do not apply to y-port 700 as the valve 710 remains unactuated and closed during storage and through the device's shelf life.

In some embodiments, the blood control valve 710 of y-port 700 greatly simplifies the clinician's technique of placing an IV catheter, and making subsequent connections thereto. For example, in some embodiments closed catheter IV system 101 eliminates the need for a separate vent plug device attached to y-port 700 to facilitate priming of the IV line 40. In other embodiments, closed catheter IV system 101 eliminates the need for tightening the vent plug onto the luer adapter, as well as the need for actuating an extension set clamp. Further, in some embodiments closed catheter IV system 101 eliminates the need for disconnecting the vent plug, being careful not to contact the blood contained within the vent plug, as well as the need to discard any contaminated vent plug. Still further, closed catheter IV system 101 eliminates the need to open the extension set clamp following catheterization.

Figure 23:
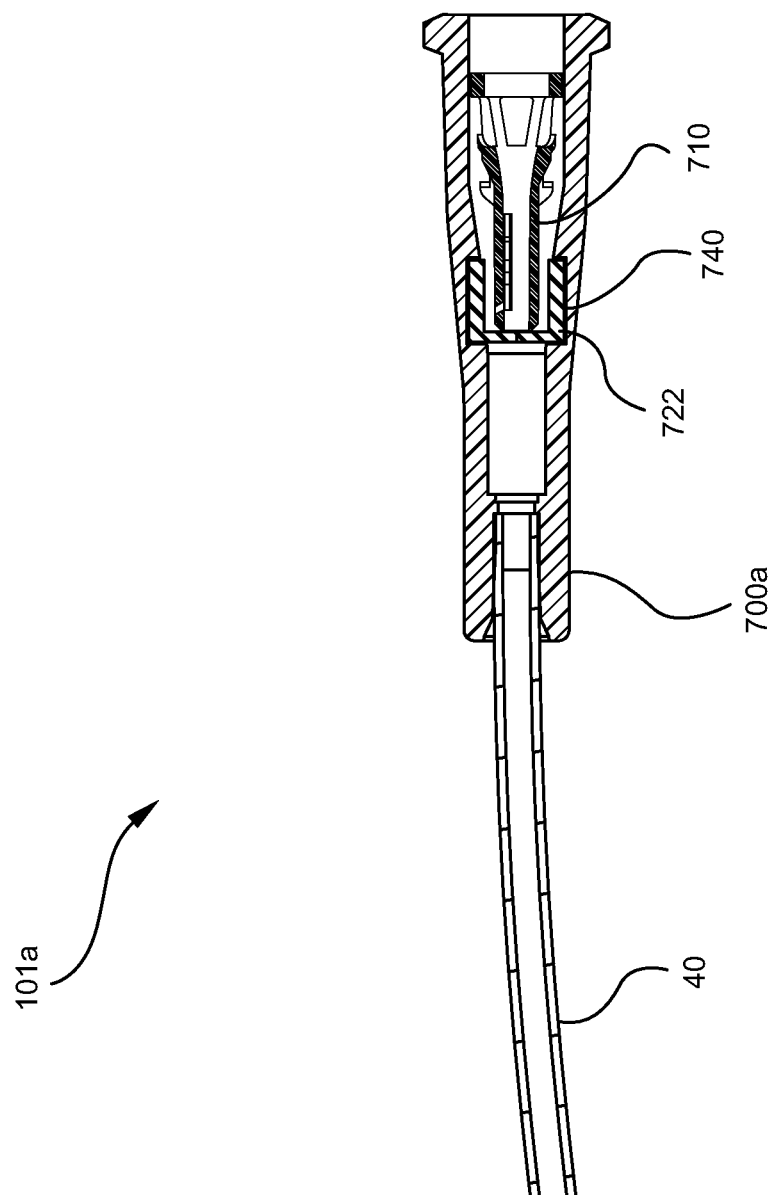
FIG. 23 is a cross-sectioned view of a vented blood control valve and single port straight luer adapter having a flow control valve mechanism in accordance with a representative embodiment of the present invention, prior to activation.
Figure 24:
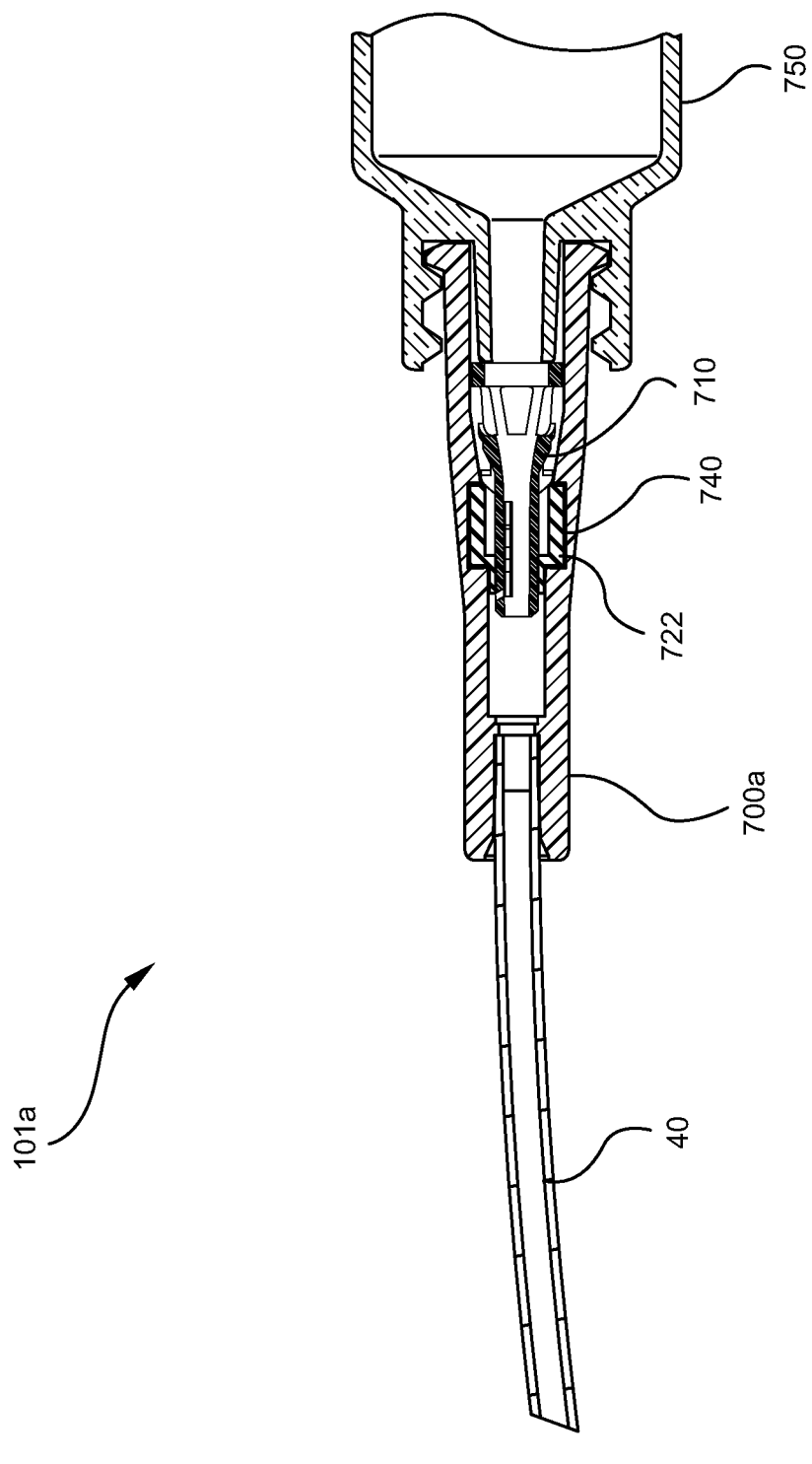
FIG. 24 is a cross-sectioned view of a vented blood control valve and single port straight luer adapter having a flow control valve mechanism in accordance with a representative embodiment of the present invention, following activation.

Referring now to FIGS. 23 and 24, in some embodiments catheter assembly 101a further comprises a single port straight luer adapter 700a configured to include a blood control valve 710 in accordance with any of the teachings of the present invention. In some embodiments, a blood control valve 710 is positioned with the straight luer adapter 700a of the closed IV catheter system 101a, as shown. In some embodiments, the blood control valve 710 comprises a septum 722 disposed within a lumen of the straight luer adapter 700a, wherein valve 710 further comprises a ventilation channel 740 interposed between the septum 722 and an inner surface of the straight luer adapter 700a to permit controlled passage of at least one of air and blood at a desired rate of flow.

Initially, the valve system comes in the unactuated position, as shown in FIGS. 23. The unactuated position allows venting of the closed system via channels 740 located between the luer adapter 700a and the valve septum 722. In some embodiments, channels 740 are sized to allow airflow, but prevent blood flow. The vented valve therefore replaces the need of including a vent plug to prime the IV line 40. During the catheterization process, blood is therefore permitted to flow into the IV line 40 until it reaches septum 722, at which point the blood flow ceases. The clinician may then simply attach any connecting device 750 to allow infusion, blood draw, or fluid delivery, as shown in FIG. 24.

In some embodiments, the clinician simply adds a cap or cover (not shown) to the luer port 720 thereby preventing contamination until later use. Upon connection of the connecting device 750, the septum activator of valve 710 is advanced through septum 722 thereby opening valve 710 to allow free flow of fluid and normal infusion therapy practices. Unlike other valve systems, long term compression set of the cannula and valve integration do not apply to straight luer 700a as the valve 710 remains unactuated and closed during storage and through the device's shelf life.

In some embodiments, the blood control valve 710 of straight luer 700a greatly simplifies the clinician's technique of placing an IV catheter, and making subsequent connections thereto, as discussed in connection with FIGS. 21 and 22, above.

Any septum described herein may be made of a variety of suitable materials and through a variety of suitable manufacturing methods. For example, the septum may be formed from liquid silicone rubber through suitable molding procedures, such as insert molding, injection molding, other molding techniques, or a combination of molding techniques. The septum 103, or any septum described herein, may also include a coating of antimicrobial substance on any of its surfaces, especially those surfaces which have contact with fluid.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A system for controlling fluid flow in a closed IV catheter assembly, comprising:
   a luer port having an inner lumen;
   a valve for controlling fluid flow through the inner lumen, the valve comprising:
      a septum disposed within a portion of the inner lumen;
      a septum activator disposed within a portion of the inner lumen adjacent to the septum, wherein a distal end of the septum activator contacts a proximal surface of the septum when the valve is in an unactuated position, and extends through the proximal surface when the valve is in an actuated position, the septum activator further including a sealing portion that extends from an exterior surface of the septum activator and contacts the surface of the inner lumen thereby preventing fluid from flowing into interstitial spaces between the septum and the sealing portion of the septum activator; and
   a ventilation channel interposed between the septum and an inner surface of the inner lumen of the luer port, the ventilation channel having a surface area and a perimeter selected to permit passage of at least one of air and blood at a desired rate of flow when the valve is in the unactuated position.

2. The system of claim 1, wherein the sealing portion comprises a sleeve attached around the septum activator.

3. The system of claim 1, wherein the sealing portion comprises a toroidal-shaped band around the outer circumference of the septum activator.

4. The system of claim 1, wherein the septum activator comprises a plurality of vents and flow diverters configured to improve circulation of the fluid within at least one of the septum activator and an interstitial space between the septum activator and the inner surface of the inner lumen.

5. The system of claim 3, wherein the septum activator further comprises a flow vent.

6. The system of claim 1, wherein the proximal surface of the septum further includes a cavity for housing the distal end of the septum activator, and wherein a distal surface of the septum is dome-shaped.

7. The system of claim 6, further comprising a relief located on an inner surface of the cavity, the relief being configured to receive a retaining feature located on the distal end of the septum activator, wherein an interaction between the retaining feature and the relief prevents removal of the septum activator from the septum.

8. The system of claim 1, wherein the ventilation channel permits the passage of air but not the passage of blood while the valve is in the unactuated position.

9. The system of claim 1, wherein the luer port comprises a y-luer port.

10. The system of claim 1, wherein the luer port comprises a straight luer port.

11. The system of claim 1, wherein the proximal surface of the septum includes a slit.

12. The system of claim 11, wherein the slit comprises a leak orifice.

13. A closed IV catheter assembly, comprising:
   a luer port having an inner lumen, the inner lumen having a proximal end, a distal end and a middle portion;
   a recess forming the middle portion of the inner lumen, the recess being configured to receive a septum, the septum forming a defeatable barrier between the proximal end and the distal end of the inner lumen;
   a ventilation channel interposed between the septum and an inner surface of the inner lumen of the luer port, the ventilation channel having a surface area and a perimeter selected to permit passage of at least one of air and blood between the proximal end and the distal end of the inner lumen, at a desired rate of flow;

a septum activator positioned within the proximal end of the inner lumen, the septum activator having a first end for biasing open a slit of the septum, and a second end having a contact surface, the septum activator further including a sealing portion that extends from an exterior surface of the septum activator and contacts the surface of the inner lumen thereby preventing fluid from flowing into interstitial spaces between the septum and the sealing portion of the septum activator; and an opening forming a proximal end of the luer port, wherein an external device is inserted through the opening to contact the contact surface of the septum activator thereby advancing the first end of the septum activator through the slit of the septum, wherein the ventilation channel permits the passage of at least one of air and blood before the first end of the septum activator is advanced through the slit of the septum.

14. The assembly of claim 13, further comprising a flow vent forming a portion of the septum activator.

15. The assembly of claim 13, wherein the septum activator further comprises a plurality of vents and flow diverters configured to improve circulation of a fluid within at least one of the septum activator pathway and an interstitial space between the septum activator and the inner surface of the luer port inner lumen.

16. The assembly of claim 13, wherein a proximal surface of the septum further includes a cavity for housing a distal end of the septum activator, and wherein a distal surface of the septum is dome-shaped.

17. The system of claim 16, further comprising a relief located on an inner surface of the cavity, the relief being configured to receive a retaining feature located on a distal end of the septum activator, wherein an interaction between the retaining feature and the relief prevents removal of the septum activator from the septum.

18. The system of claim 13, further comprising an antimicrobial coating applied to at least one of the luer port, the septum, the ventilation channel, the septum activator and the external device.

19. The system of claim 13, wherein the ventilation channel permits the passage of air but not the passage of blood before the first end of the septum activator is advanced through the slit of the septum.

20. The system of claim 13, wherein the slit further comprises a leak orifice.

* * * * *